(12) United States Patent
Burton et al.

(10) Patent No.: US 6,953,844 B2
(45) Date of Patent: *Oct. 11, 2005

(54) ISOLATION OF NEUROTROPHINS FROM A MIXTURE CONTAINING NEUROTROPHIN VARIANTS USING HYDROPHOBIC INTERACTION CHROMATOGRAPHY

(75) Inventors: Louis E. Burton, San Mateo, CA (US); Charles H. Schmelzer, Burlingame, CA (US); Joanne T. Beck, Westlake Village, CA (US)

(73) Assignee: Genentech, Inc., South San Francisco, CA (US)

( * ) Notice: Subject to any disclaimer, the term of this patent is extended or adjusted under 35 U.S.C. 154(b) by 96 days.

This patent is subject to a terminal disclaimer.

(21) Appl. No.: 10/782,261

(22) Filed: Feb. 18, 2004

(65) Prior Publication Data

US 2004/0138431 A1 Jul. 15, 2004

Related U.S. Application Data

(63) Continuation of application No. 10/072,681, filed on Feb. 8, 2002, now Pat. No. 6,812,330, which is a continuation of application No. 09/675,503, filed on Sep. 29, 2000, now Pat. No. 6,423,831, which is a continuation of application No. 09/363,573, filed on Jul. 29, 1999, now Pat. No. 6,184,360, which is a continuation of application No. 08/970,865, filed on Nov. 14, 1997, now Pat. No. 6,005,081.
(60) Provisional application No. 60/030,838, filed on Nov. 15, 1996, and provisional application No. 60/047,855, filed on May 29, 1997.

(51) Int. Cl.[7] .............................. C07K 3/14; C12P 21/06
(52) U.S. Cl. ....................... 530/399; 530/324; 530/350; 530/412; 530/416; 530/417; 435/69.1; 435/69.4; 435/70.1; 435/71.1
(58) Field of Search ................................. 530/399, 324, 530/350, 412, 416, 417; 435/69.1, 69.4, 70.1, 71.1

(56) References Cited

U.S. PATENT DOCUMENTS

| | | |
|---|---|---|
| 4,407,744 A | 10/1983 | Young |
| 4,565,785 A | 1/1986 | Gilbert et al. |
| 4,673,641 A | 6/1987 | George et al. |
| 4,710,473 A | 12/1987 | Morris |
| 4,738,921 A | 4/1988 | Belagaje et al. |
| 4,795,706 A | 1/1989 | Hsiung et al. |
| 5,082,774 A | 1/1992 | Heinrich et al. |
| 5,169,762 A | 12/1992 | Gray et al. |
| 5,210,185 A | 5/1993 | Delli Valle et al. |
| 5,235,043 A | 8/1993 | Collins et al. |
| 5,272,063 A | 12/1993 | Chan et al. |
| 5,288,622 A | 2/1994 | Gray et al. |
| 5,364,769 A | 11/1994 | Rosenthal |
| 5,389,529 A | 2/1995 | Panayotatos et al. |
| 5,438,121 A | 8/1995 | Barde et al. |
| 5,453,361 A | 9/1995 | Yancopoulos et al. |
| 5,488,099 A | 1/1996 | Persson et al. |
| 5,512,661 A | 4/1996 | Shooter et al. |
| 5,606,031 A | 2/1997 | Lile et al. |
| 5,639,664 A | 6/1997 | Iwane et al. |
| 5,702,906 A | 12/1997 | Rosenthal |
| 5,705,617 A | 1/1998 | Persson et al. |
| 5,728,803 A | 3/1998 | Urfer et al. |
| 5,733,875 A | 3/1998 | Martin |
| 5,798,448 A | 8/1998 | Caras et al. |
| 5,830,858 A | 11/1998 | Rosenthal |
| 5,843,914 A | 12/1998 | Johnson, Jr. et al. |
| 6,005,081 A * | 12/1999 | Burton et al. ............. 530/399 |
| 6,184,360 B1 * | 2/2001 | Burton et al. ............. 530/399 |
| 6,423,831 B1 * | 7/2002 | Burton et al. ............. 530/399 |

FOREIGN PATENT DOCUMENTS

| | | |
|---|---|---|
| EP | 121338 | 10/1984 |
| EP | 450386 A2 | 10/1991 |
| EP | 414151 | 3/1995 |
| EP | 685490 | 12/1995 |
| WO | WO 92/05254 | 4/1992 |
| WO | WO 92/22665 | 12/1992 |
| WO | WO 95/16701 | 6/1995 |
| WO | WO 95/30686 | 11/1995 |
| WO | WO 95/33829 | 12/1995 |

OTHER PUBLICATIONS

Angeletti, "Nerve Growth Factor from Cobra Venom" *Proc. Natl. Acad. Sci. USA* 65(3):668–674 (1970).
Angeletti, et al. "Nerve Growth Factor From Mouse Submaxillary Gland: Amino Acid Sequence" *Proc. Natl. Acad. Sci. USA* 68(10):2417–2420 (1971).
Angeletti, et al. "Purification Characterization, and Partial Amino Acid Sequence" *Biochem* 15:26–34 (1976).
Barnett, et al., "Physicochemical Characterization of Recombinant Human Nerve Growth Factor Prodcued in Insect Cells with a Baculovirus Vector" *J. of Neurochemistry* 57(3):1052–1061 (1991).
Belew, et al., "Chick Embryo Nerve Growth Factor" *Exp. Cell Res.,* 167:550–558 (1988).
Berkmeier, et al., "Neurotrophin–5: A Novel Neurotrophic Factor That Activates trk and trkB" *Neuron* 7:857–865 (Nov. 1991).
Bigon, etl al., "Large Scale Purification and Immunological Characterization of Human Placental Nerve Growth" *Neurochemical Research* 15(12):1197–1202 (1990).
Bocchini, et al., "The Nerve Growth Factor: Purification as a 30,000–Molecular–Weight Protein" *Proc. Natl. Acad. Sci. USA* 64:787–794 (1969).

(Continued)

*Primary Examiner*—Jon Weber
*Assistant Examiner*—Abdel A. Mohamed
(74) *Attorney, Agent, or Firm*—Ginger R. Dreger; Atulya R. Agarwal; James A. Fox

(57) ABSTRACT

Methods are provided for large scale purification of neurotrophins, including mature NGF, suitable for clinical use. The methods provide means to separate neurotrophins from various less desirable misprocessed, misfolded, size, glycosylated, or charge forms. Compositions of neurotrophins, including mature NGF, substantially free of these variants are also provided.

29 Claims, 16 Drawing Sheets

OTHER PUBLICATIONS

Bradshaw, "Nerve Growth Factor" *Ann. Rev. Biochem,* 47:191–216 (1978).

Bruce, et al., "Production and Characterization of Biologically Active Recombinant Human Nerve Growth Factor" *Neurobiology* 10:89–94 (1988).

Buj–Bello, et al., "GDNF is an Age–Specific Survival Factor for Sensory and Automic Neurons" *Neuron* 15:821–828 (1995).

Burton, et al., "Activity and Biospecificity of Proteolyzed Forms and Dimeric Combinsations of Recombianant Huamna and Murine Nerve Growth Factor" *J. Neurochem.* 59(5): 1937–1945 (1992).

Callegaro, L., et al. "Biological and Immunochemical Properties of Recombinant Human NGF" *Trophic Factors and the Nervous System,* L. A. Horrocks, et al., New York: Raven Press, Ltd. pps. 75–82 (1990).

Chapman, et al., "The Isolation and Characterization of Nerve Growth Factor from the Prostate Gland of the Guinea Pig" *European Journal of Biochemistry* 115:347–351 (1981).

De Young, et al., "RhNGF Slow Unfolding is not Due to Proline Isomerization: Possibility of a Cystine Knot Loop–Threading Mechanism" *Protein Sci.* 5(8):1554–1566 (1996).

Dicou, et al., "Synthesis of Chimeric Mouse β–Nerve Growth Factor Precursor and Human –Nerve Growth Factor in *Escherichia coli*:Immunological Properties" *Journal of Neuroscience Research* 22:13–19 (1989).

Edwards, et al., "Processing and Secretion of Nerve Growth Factor: Expression in Mammalian Cells with a Vaccina Virus Vector" *Molecular & Cellular Biology* 8(6):2456–2464 (1988).

Emfors, et al., "Molecular Cloning and Neurotrophic Activities of a Protein With Structural Similarities to Nerve Growth Factor: Developmental and Topgraphical Expression in the Brian" *Proc. Natl Acad. Sci. USA* 87:5454–5458 (Jul. 1990).

Goldstein, et al., "Isolation of Human Nerve Growth Factor From Placental Tissue" *Neurochemical Research* 3:175–183 (1978).

Hallbook, et al., "Evolutionary Studies of the Nerve Growth Factor Family Reveal a Novel Member Abundantly Expressed in Xenopus Ovary" *Neuron* 6 :845–858 (May 1991).

Heinrich, et al., "Nerve Growth Factor (NGF) is Present in Human Placenta and Semen, But Undectable in Normal and Pagel's Disease Blood: Measurements with an Anti–Mouse NGF Enzyme Immunoassay Using a Recombinant Human NGF Reference" *Biochemical and Biophysical Research Communications* 155(1):482–486.

Henerson, et al., "GDNF: A Potent Survival Factor for Motneurons Present in Peripheral Nerve and Muscle" *Science* 266:1062–1064 (1994).

Hohn, et al., "Identification and Characterization of a Novel Member of the Nerve Growth Factor/Brain–derved Neurotrophic Factor Family" *Nature* 344 :339–341 (Mar. 22, 1990).

Ip., et al., "Mammalian Neurotrophin–4: Structure, Chromosomal Localization, Tissue Distribution, and Receptor Speicficity" *Proc. Natl. Acad. Sci USA* 89 :3060–3064 (Apr. 1992).

Iwai, et al., "Deoxyribonucleic acids and Related Compounds. XXII. Synthesis of Genes for Human Nerve Growth Factor and Its Fused and Its Fused Protein" *Chem. Pharm. Bull.* 34(11):4724–4703 (1988).

Jones, et al., "Molecular Cloning of a Human Gene that is a Member of the Nere Growth Factor Family" *Proc. Natl. Acad Sci USA* 87:8050–8064 (1990).

Jongstra–Bilen, et al., "The in vitro processing of the NGF Precursors by the γ–subunit of the 7s NGF complex" *Molecular Brain Research* 5:159–169 (1989).

Kahle, et al., "The Amino Termiunus of Nerve Growth Factor Is Involved in the Interaction with the Receptor Tyrosine Kinase p140$^{trk}$" *Journal of Biological Chemistry* 267(32):22707–22710 (Nov. 15, 1991).

Kaisho, et al., "Cloning and expression of a cDNA encoding an oval human neurotrophic factor" *FEBS Letters* 266(1,2): 187–191 (Jun. 1990).

Kanaya, et al., "Synthesis and Secretion of Human Nerve Growth Factor by *Saccharomces Cerevisiae*" *Gene* 83:65–74 (1989).

Kotzbauer, et al., "Neurturin, a relative of glial–cell–line–derived neurotophic factor" *Nature* 384:467–470 (1998).

Leibrock, et al., "Molecular Cloning and Expression of Brain–Derived Neurotropic Factor" *Nature* 341:149–152 (Sep. 14, 1989).

Lin, et al., "GDNF: A Glial Cell Line–Derived Neurotropic Factor for Midbrain Dopaminergic Neurons" *Science* 260:1130–1132 (1993).

Malsano, et al., "Synthesis of New Hydrophobic Adsorbents Based on Homologous Series of Uncharged Alkylsulphide Agarose Derivatives" *Journal of Chromatography,* 321:305–317 (1985).

Maisonpierre, et al., "Neurotrophin–3: A Neurotrophic Factor Related to NGF and BDNF" *Science* 247:1446–1451 (Mar. 23, 1990).

Mobley, et al., "Characterization of Isolation of Proteolytically Modified Nerve Growth Factor" *Biochemistry* 15:5543–5552 (1976).

Norrgren, et al.; "Release of Nerve Growth Factor by Human Glial Cells in Culture" *Experimental Cell Research* 130:31–39 (1980).

Pantazis, "Nerve Growth Factor Synthesized by Mouse Fibroblast Cells in Culture: Absence of α and γ Subunits" *Biochemistry* 22:4264–4271 (1983).

Rosenthal, et al., "Primary Structure and Biological Activity of a Novel Human Neurotrophic Factor" *Neuron* 4:767–773 (May 1990).

Rusenko, et al., "Interaction of [$^{125}$I]. Nerve Growth Factor with Acidic Proteins" *Neurochemical Research* 6(3):287–300 (1981).

Saboori, et al., "Nerve Growth Factor: Biosynthetic Products of the Mouse Salivary Glands. Characterization of Stable High Molecular Weight and 32.000–Dalton Nerve Growth Factors" *Biochemistry* 25:5565–5571 (1986).

Schmeizer, et al. "Biochemical Characterization of Recombinant Human Nerve Growth Factor" *Journal of Neurochemistry* 59(5):1675–1683 (1992).

Scott, et al., "Isolation and nucleotide sequence of a cDNA encoding the precursor of mouse nerve growth factor" *Nature* 302:538–540 (1983).

Shih, et al., "Mutagenesis Identifies Amino–terminal Residues of Nerve Growth Factor Necessary for Trk Receptor Binding and Biological Activity" *Journal of Biological Chemistry* 269:27679–27686 (1994).

Suda, et al., "Nerve Growth Factor in Mouse and Rat Serum: Correlation Between Bioassay and Radioimmunoassay Determination" *Proc. Natl. Acad. Sci. USA* 75(8):4042–4046 (1978).

Ulrich, et al., "Human β–Nerve growth factor Gene Sequence Highly Homologous to That of Mouse" *Nature,* 303:821–825 (Jun. 1983).

Ulrich, et al., "Sequence Homology of Human and Mouse B–NGF Subunit Genes" *Symp. On Quan. Biol.* 48:435–442 (1983).

Urfer, et al., "The Binding Epitopes of Neurotrophin–3 to its Receptros trkC and gp75 and the Design of a Multifuncational Human Neurotrophin" *EMBO Journal* 13(24):5896–5909 (1994).

Varon, et al., "The Isolation of the Mouse Nerve Groth Factor Protein in a High Molecular Weigh Form" *Biochemistry* 6(7):2202–2209 (1967).

Walker, et al., "Human Nerve Growth Factor: Lack of Immunocross–activity with Mouse Nerve Growth Factor" *Life Sciences* 26:195–200 (1980).

* cited by examiner

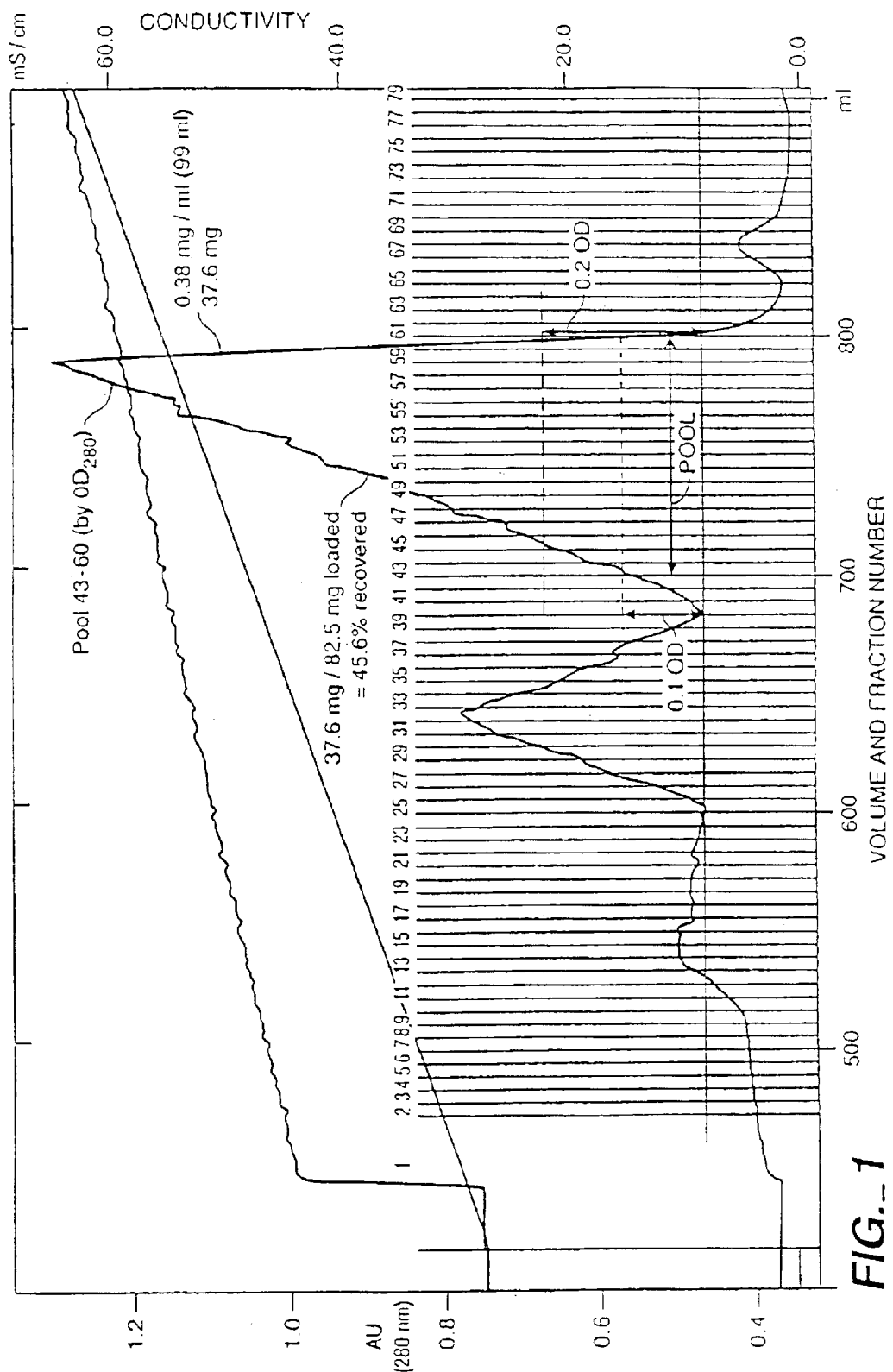
FIG._1

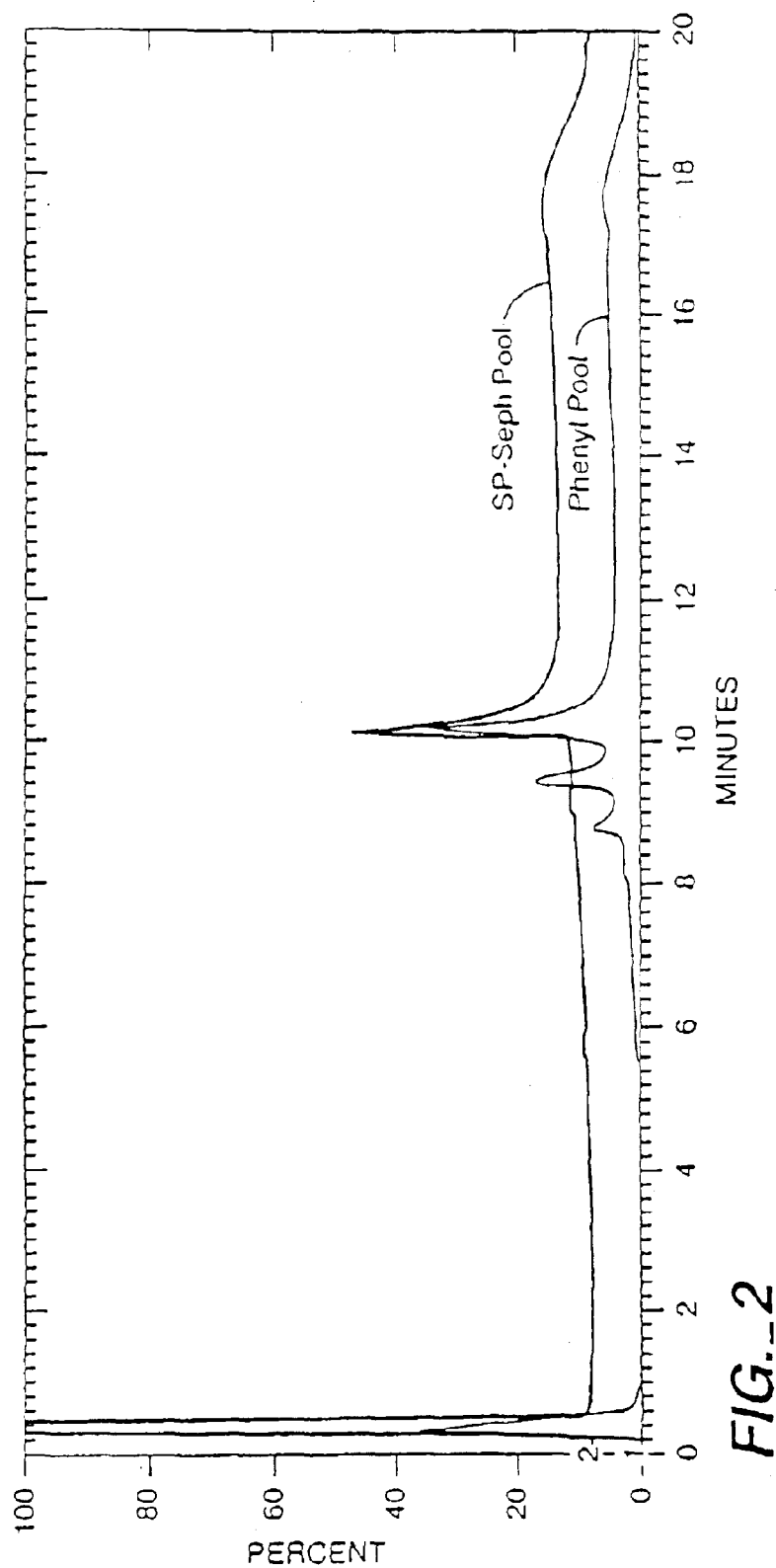
FIG._2

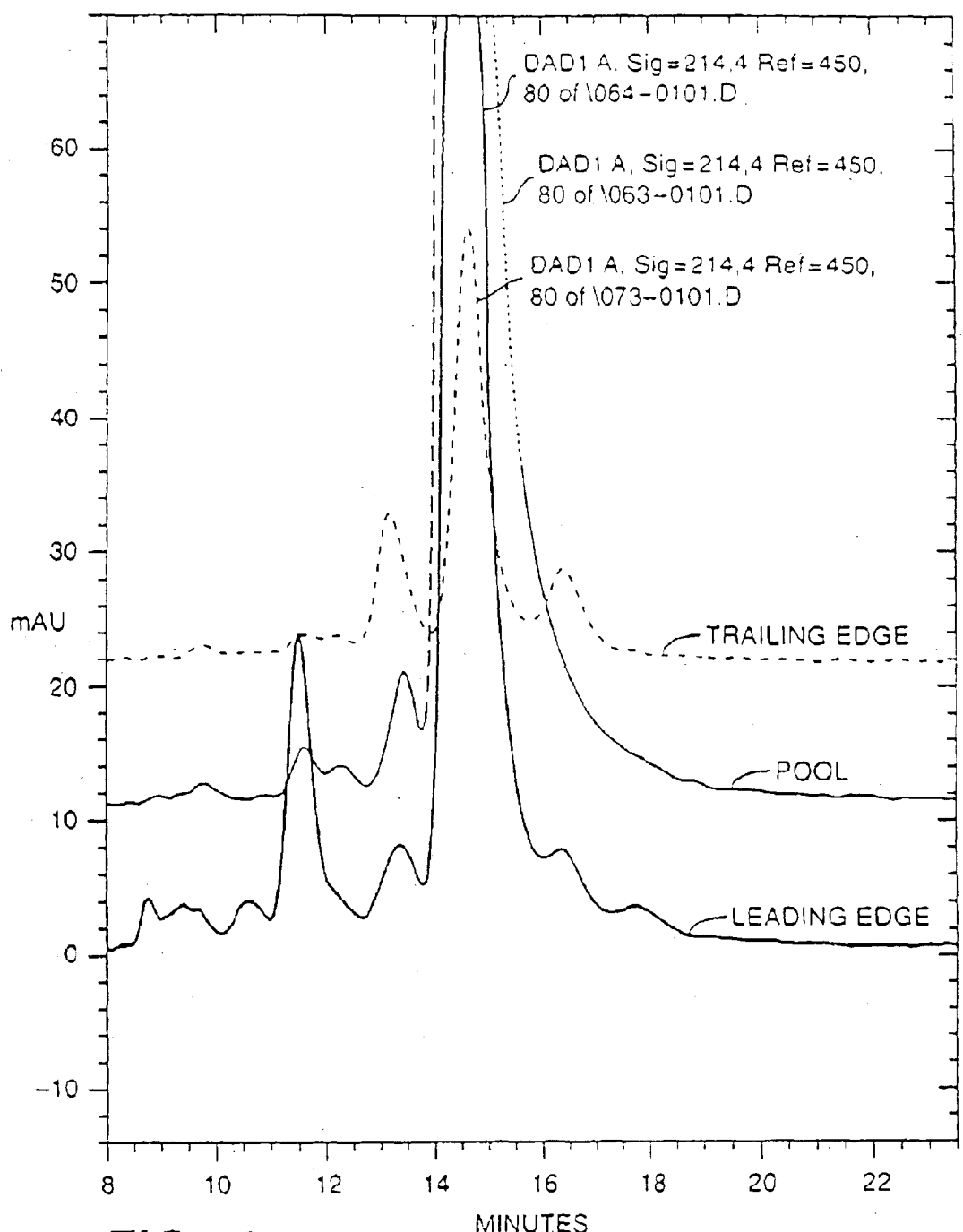
FIG._3

-120
↓

MSMLFYTLITAFLIGIQAEPHSESNVPAGHTIPQVHWTKLQHSLDTALRRAR

SAPAAAIAARVAGQTRNITVDPRLFKKRRLRSPRVLFSTQPPREAADTQDLD

1
↓

FEVGGAAPFNRTHRSKRSSSHPIFHRGEFSVCDSVSVWVGDKTTATDIKGKE

VMVLGEVNINNSVFKQYFFETKCRDPNPVDSGCRGIDSKHWNSYCTTTHTFV

120
↓

KALTMDGKQAAWRFIRIDTACVCVLSRKAVRRA

*FIG._4*

```
rhNGF    1  --SSSHPIFHRGEFSVCDSVSVWV--GDKTTATDIKGKEVMVLGEVN-IN
muNGF    1  --SSTHPVFHMGEFSVCDSVSVWV--GDKTTATDIKGKEVTVLAEVN-IN
BDNF     1  ---HSDPA-RRGELSVCDSISEWVTAADKKTAVDMSGGTVTVLEKVP-VS
NT-3     1  ---YAEHKSHRGEYSVCDSESLWV--TDKSSAIDIRGHQVTVLGEIK-TG
NT-4/5   1  GVSETAPASRRGELAVCDAVSGWV--TDRRTAVDLRGREVEVLGEVPAAG rhNGF   46  NSVFKQYFFETK CRDPNPVD-------SGC RGIDSKHWNSYCTTTHTFVK
muNGF   46  NSVFRQYFFETK CRASNPVE-------SGC RGIDSKHWNSYCTTTHTFVK
BDNF    46  KGQLKQYFYETK CNPMGYTK-------EGC RGIDKRHWNSQCRTTQSYVR
NT-3    45  NSPVKQYFYETR CKEARPVK-------NGC RGIDDKHWNSQCKTSQTYVR
NT-4/5  49  GSPLRQYFFETR CKADNAEEGGPGAGGGGC RGVDRRHWVSECKAKQSYVR rhNGF   89  ALTMD-GKQAAWRFIRIDTA CVC VLSRKAVRRA
muNGF   89  ALTTD-EKQAAWRFIRIDTA CVC VLSRKATRRG
BDNF    89  ALTMDSKKRIGWRFIRIDTS CVC TLTIKRGR--
NT-3    88  ALTSENNKLVGWRWIRIDTS CVS ALSRKIGRT-
NT-4/5  99  ALTAHAQGRVGWRWIRIDTA CVC TLLSRTGRA-
```

*FIG._5*

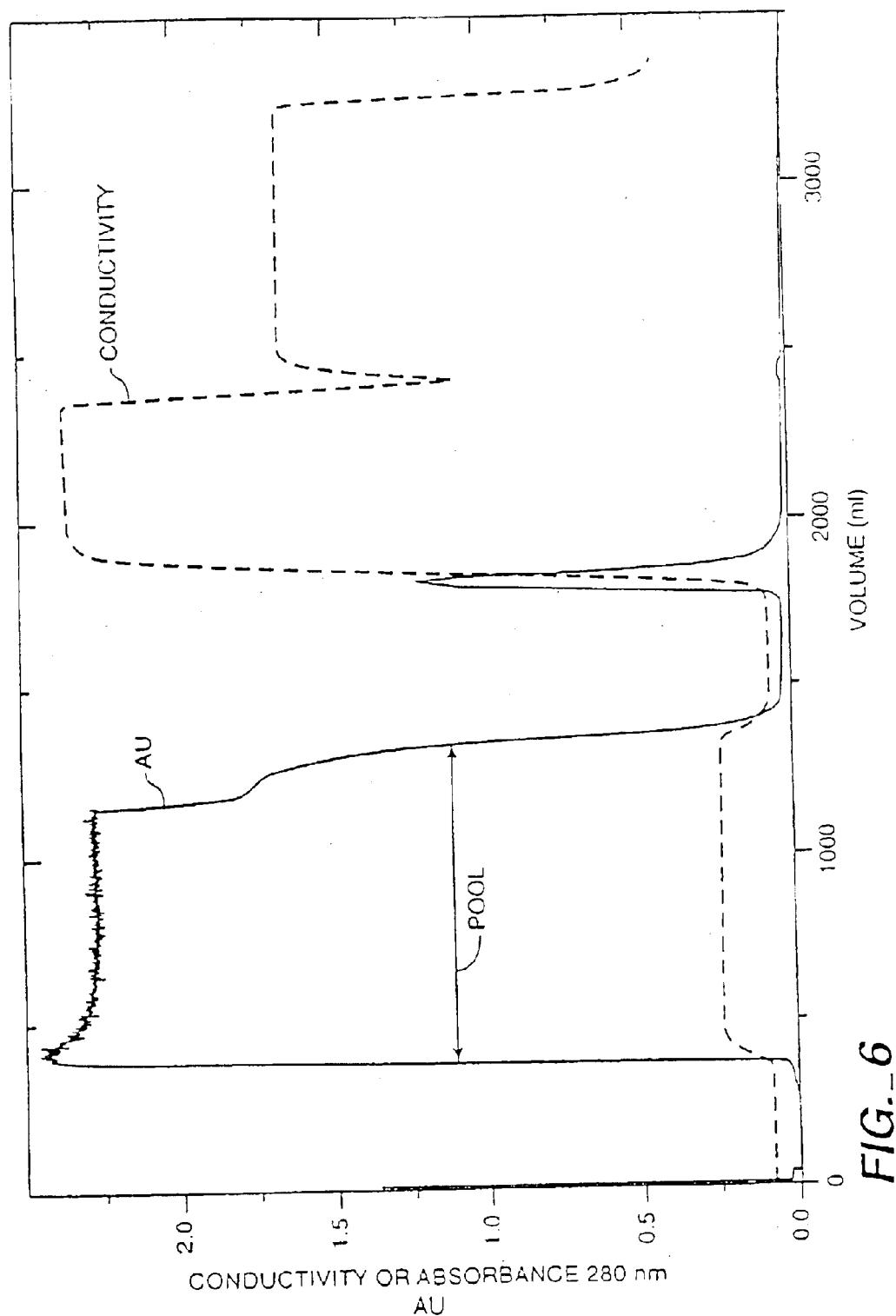
FIG._6

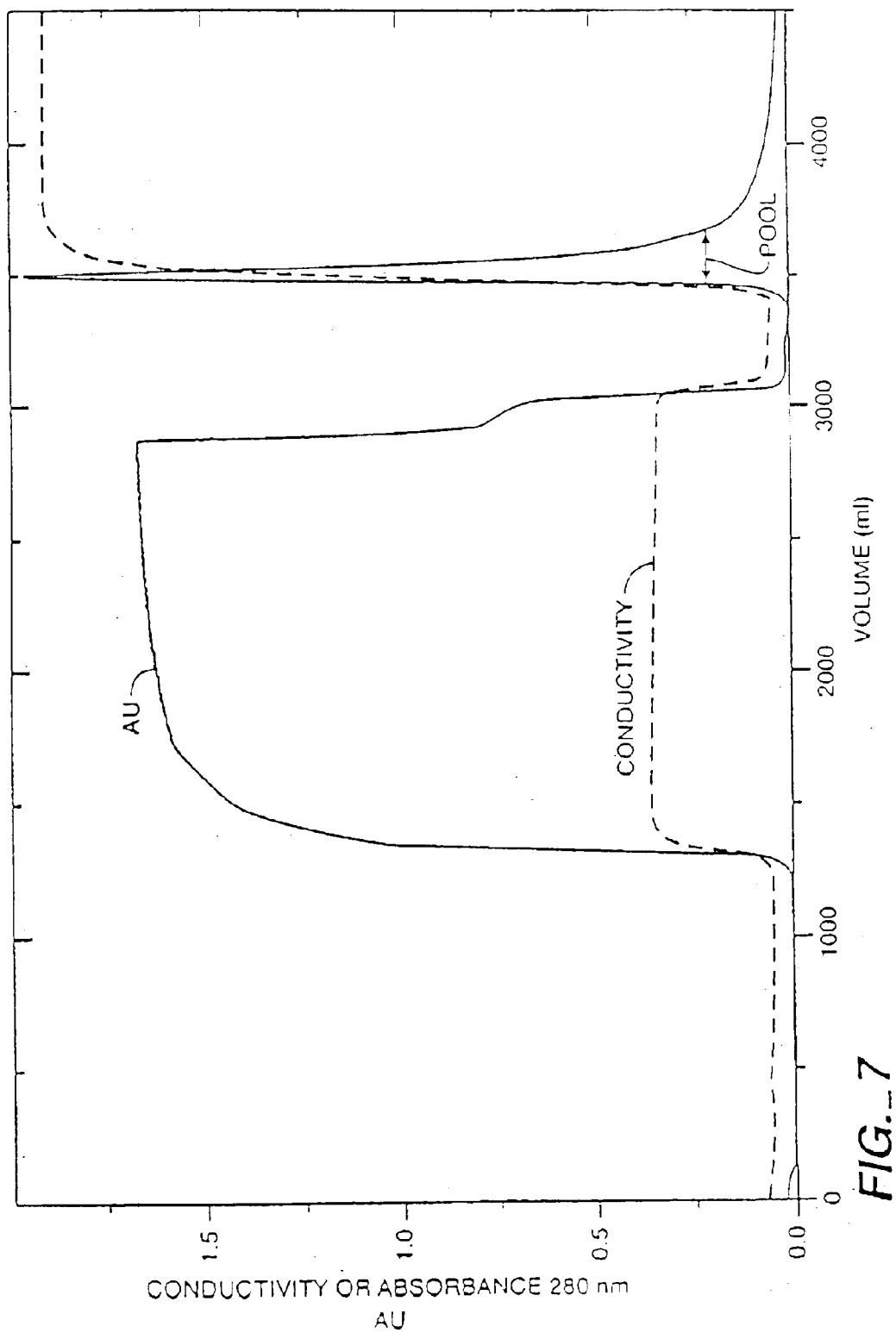
FIG._7

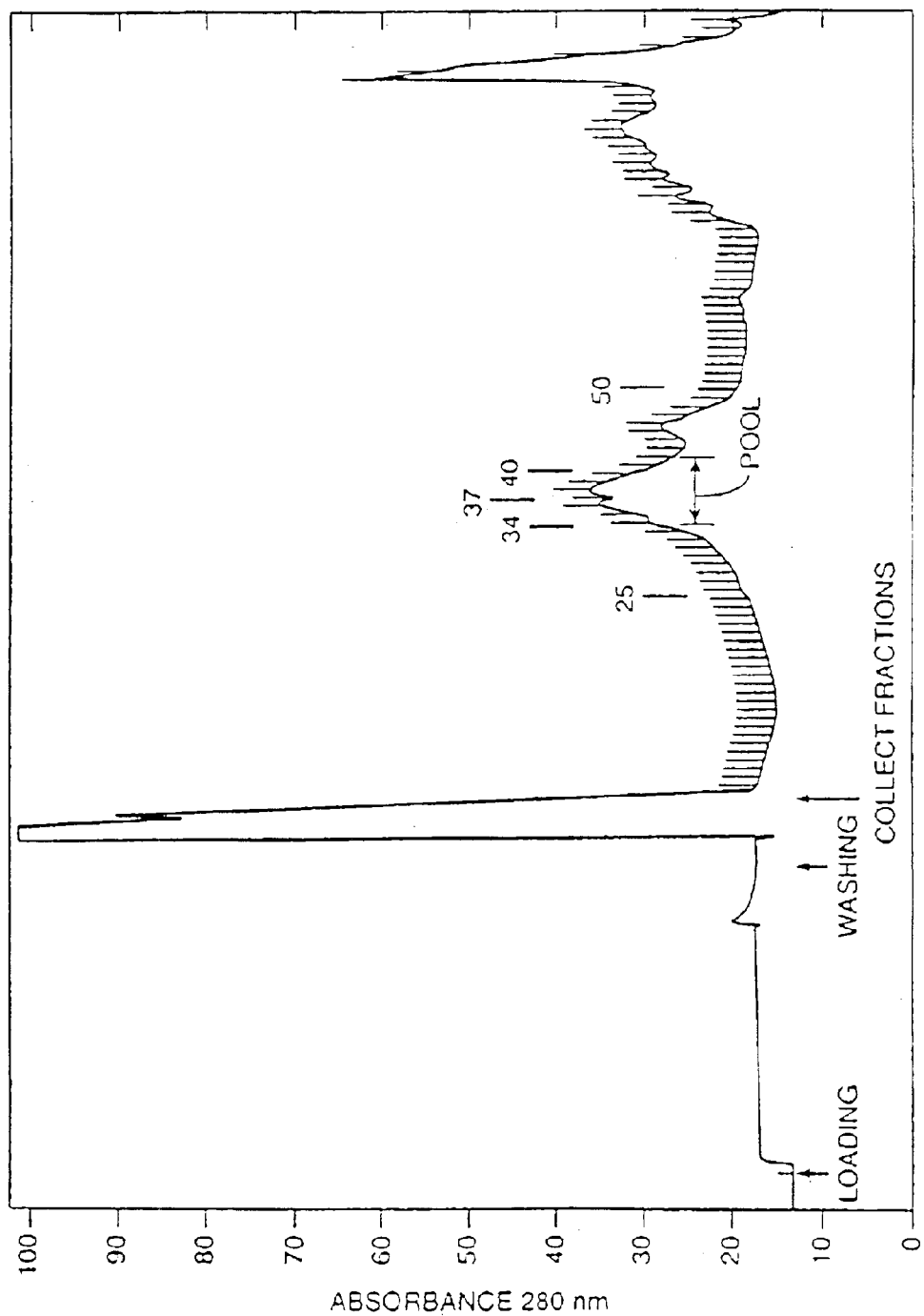
FIG._8

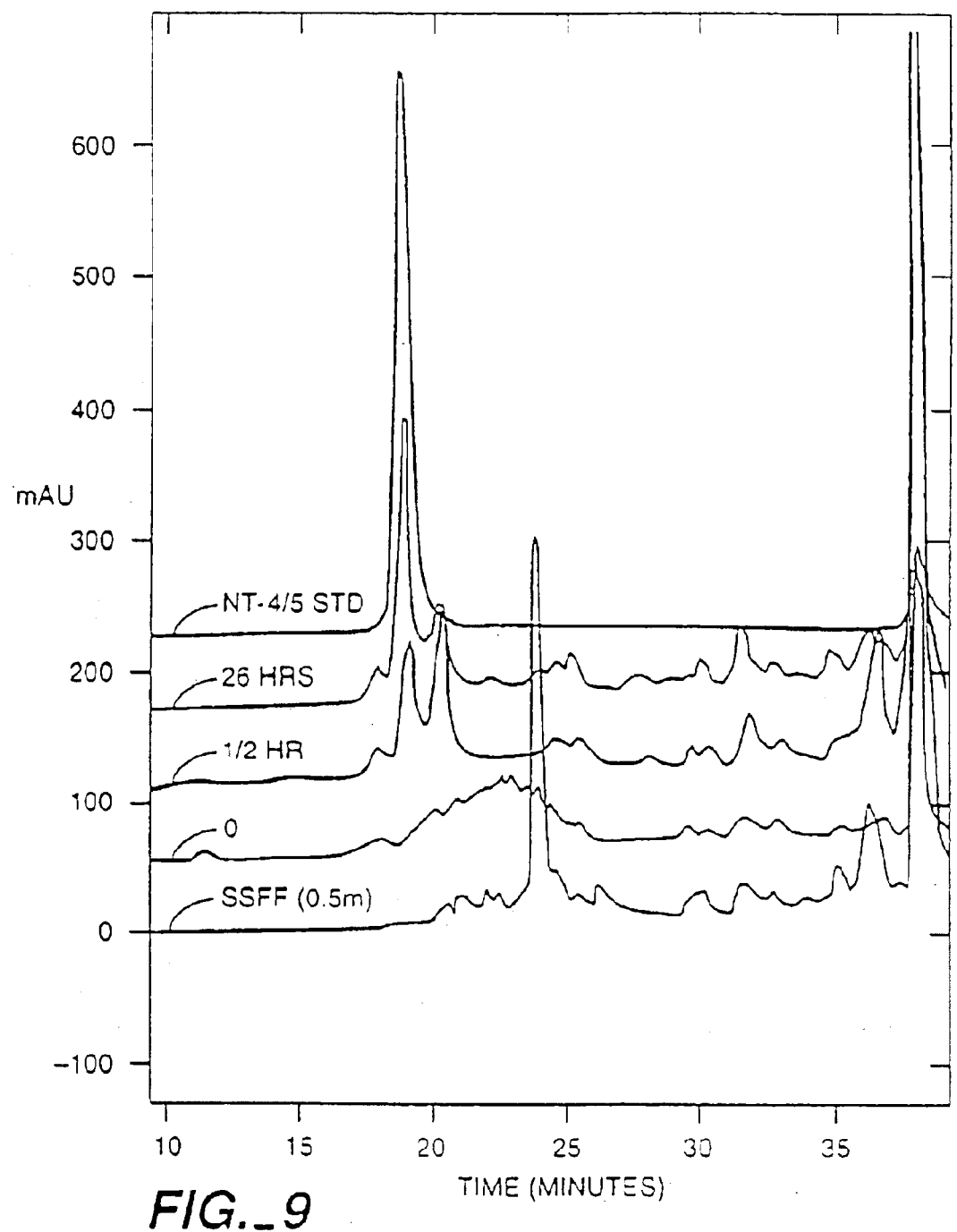
FIG._9

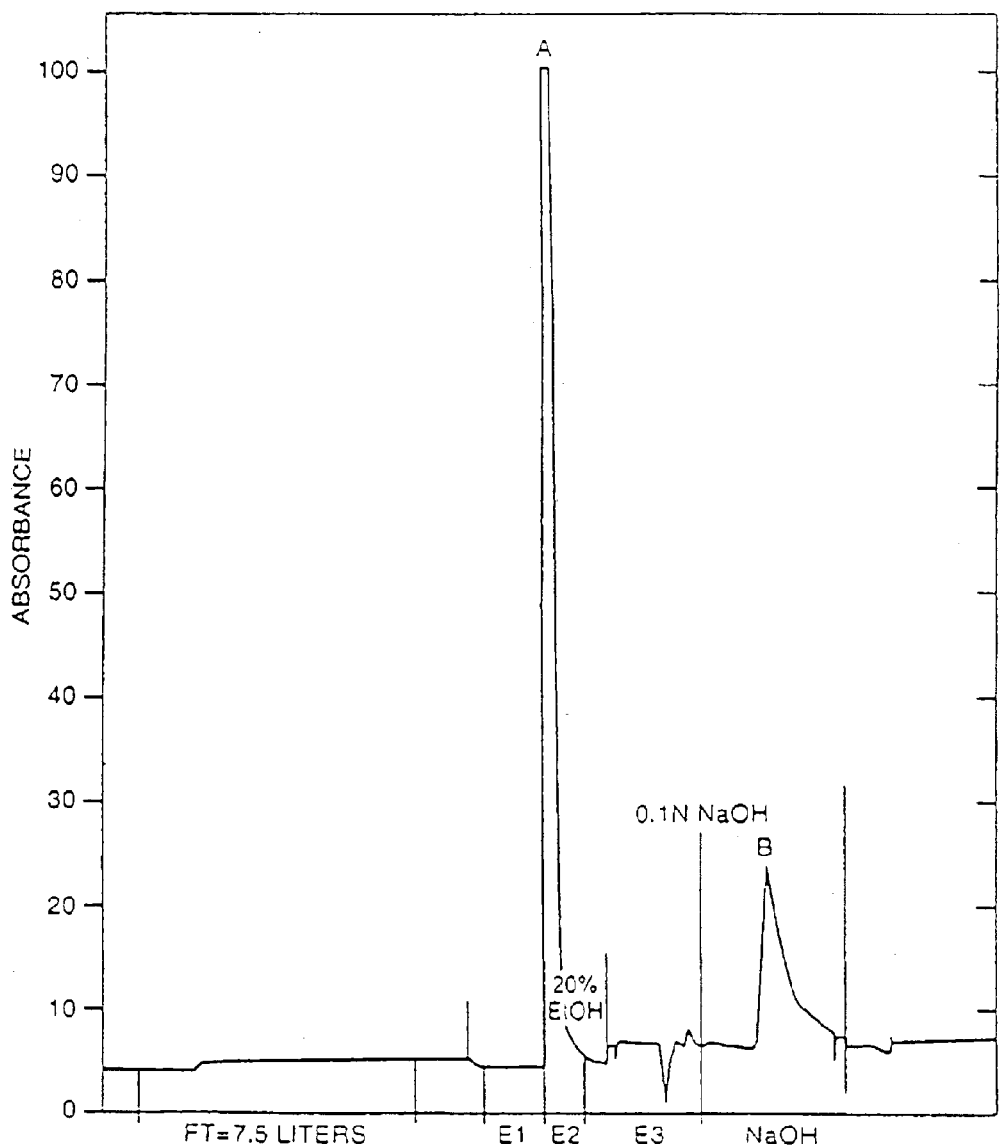
FIG._10

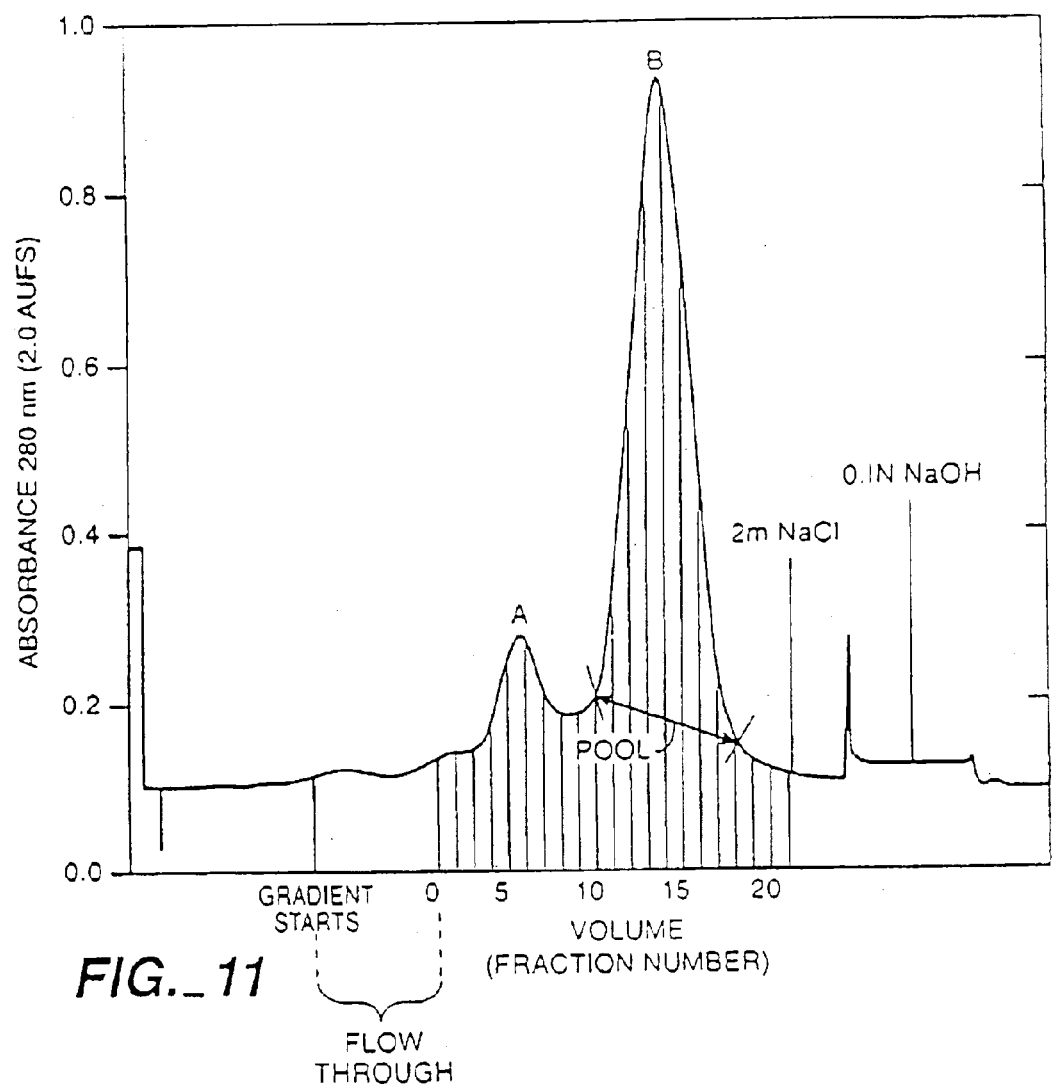
FIG._11

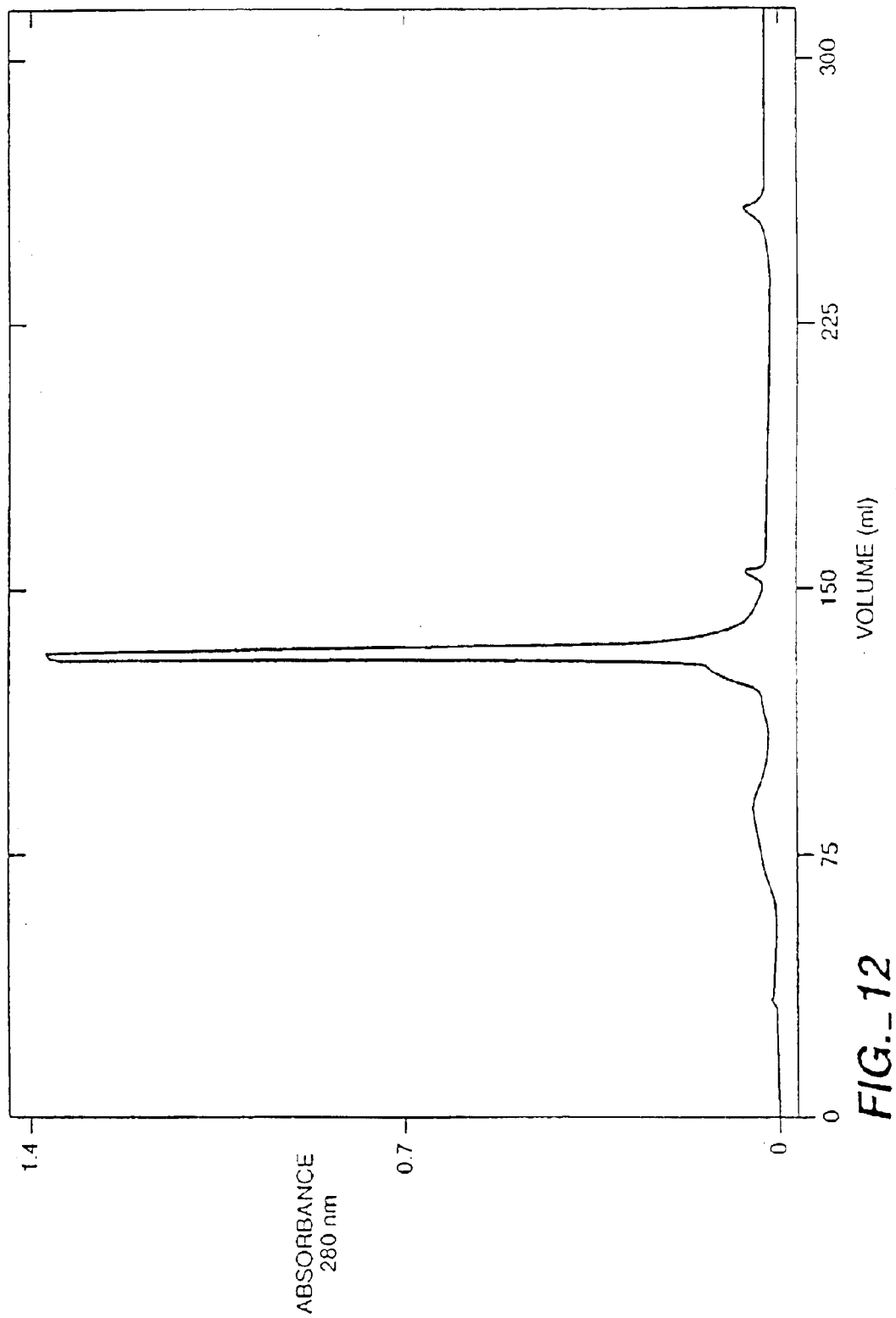
FIG._12

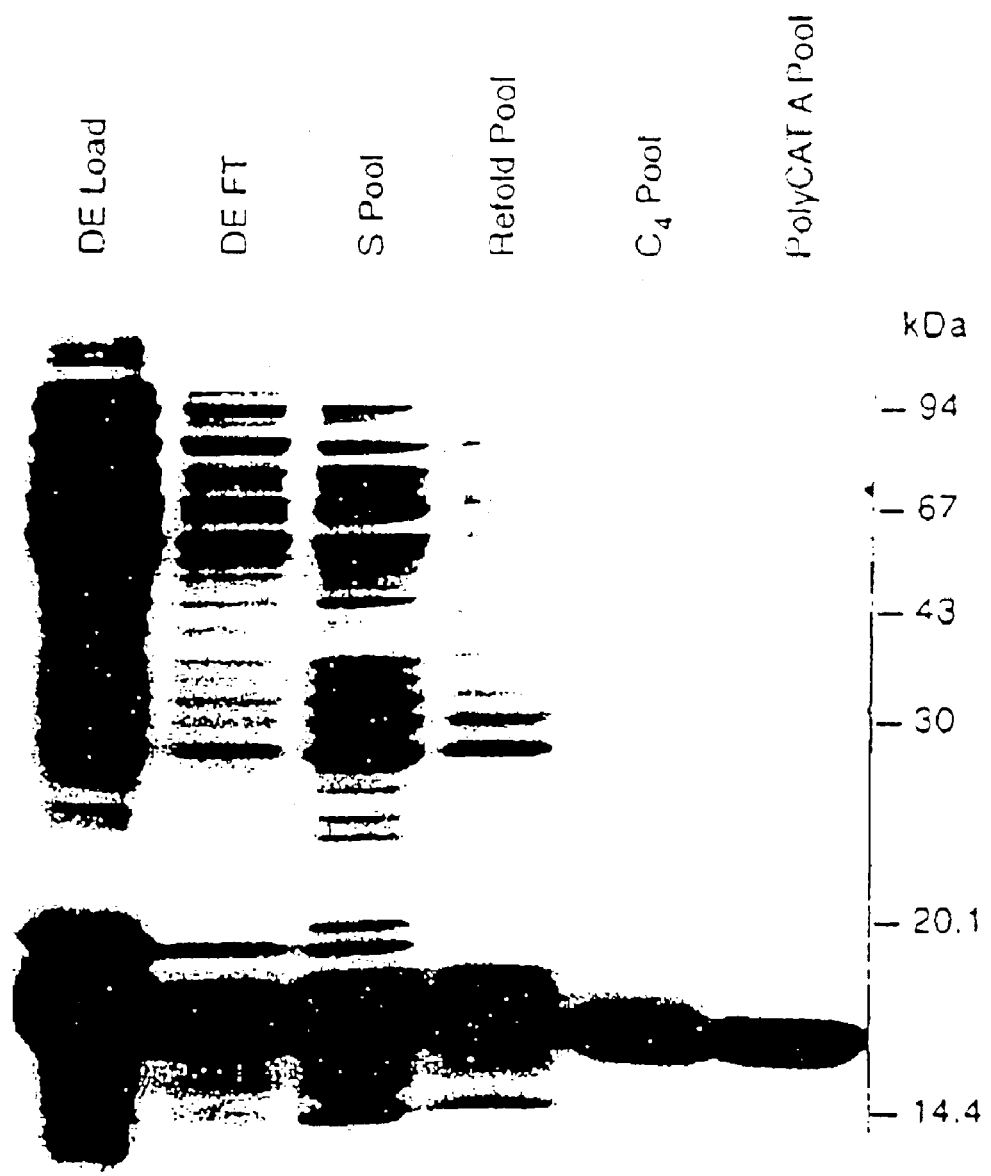
FIG._13

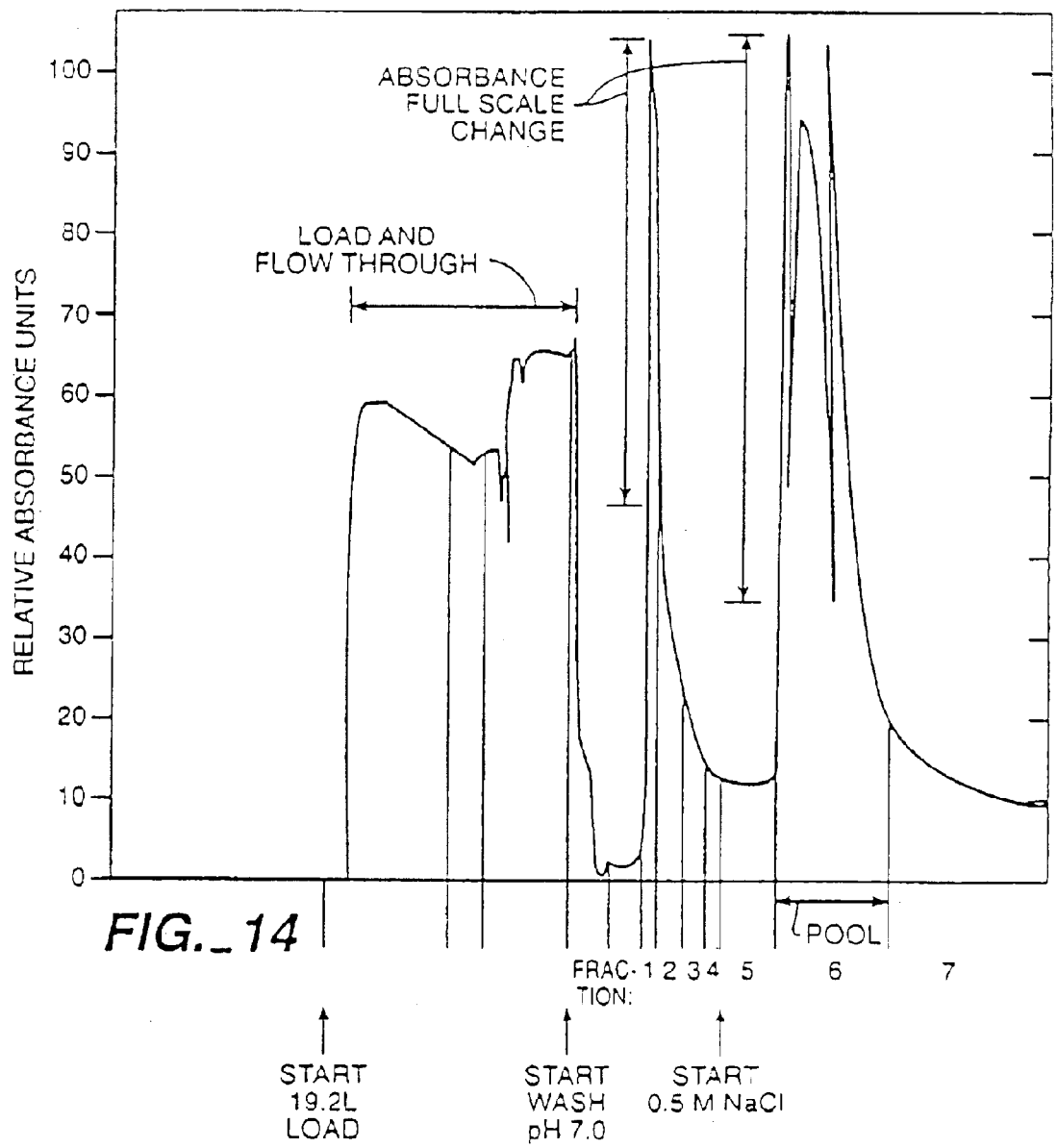
FIG._14

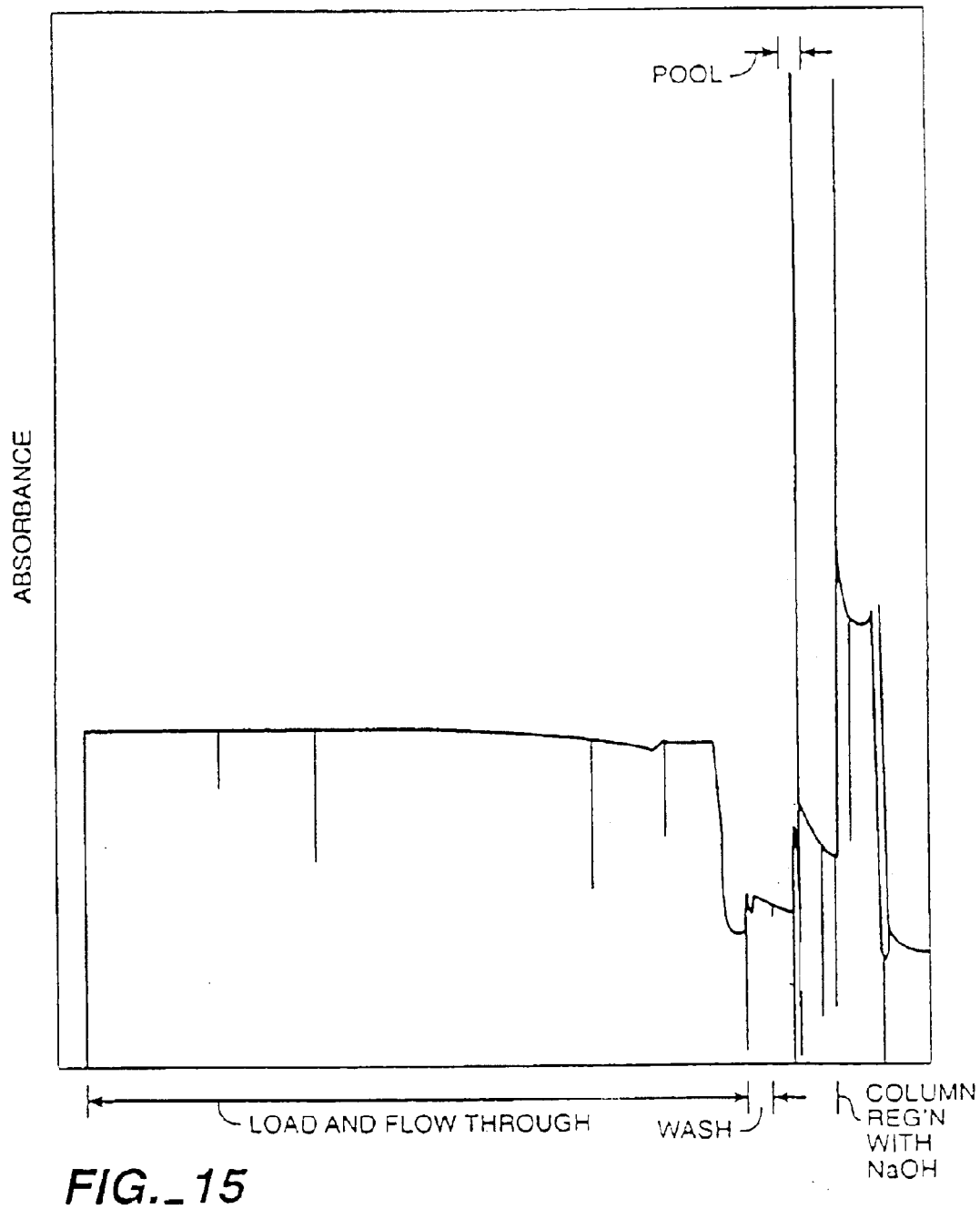
FIG._15

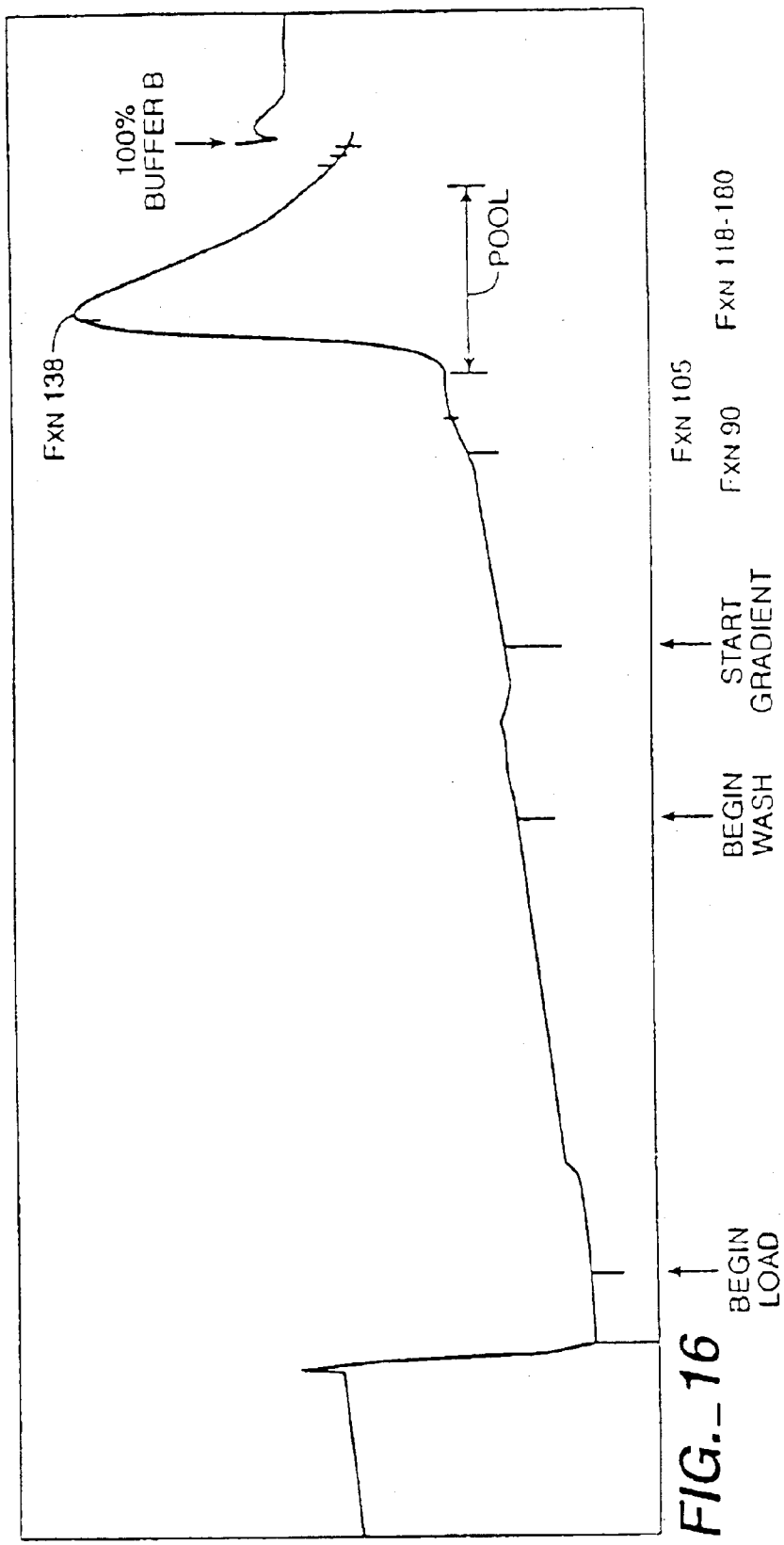
FIG.—16

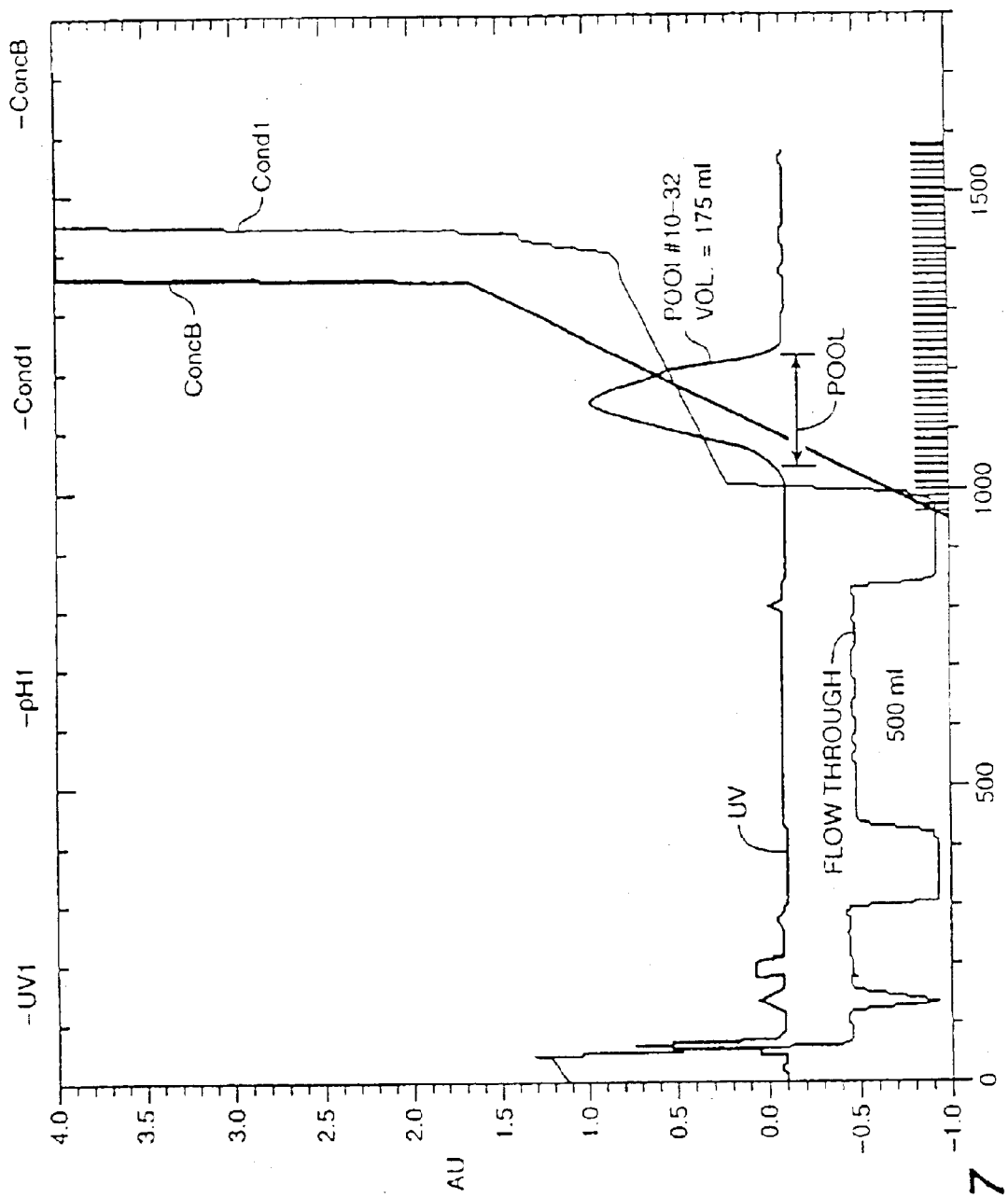
FIG._17

ISOLATION OF NEUROTROPHINS FROM A MIXTURE CONTAINING NEUROTROPHIN VARIANTS USING HYDROPHOBIC INTERACTION CHROMATOGRAPHY

RELATED APPLICATIONS

This is a continuation of application Ser. No. 10/072,681, filed Feb. 8, 2002, now U.S. Pat. No. 6,812,330 which is a continuation of application Ser. No. 09/675,503, filed on Sep. 29, 2000, now U.S. Pat. No. 6,423,831, which is a continuation of application Ser. No. 09/363,573, filed on Jul. 29, 1999, now U.S. Pat. No. 6,184,360, which is a continuation of application Ser. No. 08/970,865 filed on Nov. 14, 1997, now U.S. Pat. No. 6,005,081 which claims priority under USC Section 119(e) to Provisional Application Ser. No. 60/030,838 filed on Nov. 15, 1996 and Provisional Application Ser. No. 60/047,855 filed May 29, 1997, all of which are incorporated herein by reference.

FIELD OF THE INVENTION

This invention relates to an improved method for purifying neurotrophins, particularly those in the NGF-family, more particularly nerve growth factor (NGF) and neurotrophin-4/5 (NT-4/5), and neurotrophin-3 (NT-3) from variants, impurities, and contaminants associated therewith, particularly when produced by bacterial or mammalian cell fermentation.

BACKGROUND OF THE INVENTION

The production of large quantities of relatively pure, biologically active polypeptides and proteins is important economically for the manufacture of human and animal pharmaceutical formulations, enzymes, and other specialty chemicals. For production of many proteins, recombinant DNA techniques have become the method of choice because large quantities of exogenous proteins can be expressed in mammalian host cells and, bacteria, and other host cells.

The primary structure of a mammalian NGF (mouse NGF) was first elucidated by Angeletti and Bradshaw, Proc. Natil. Acad. Sci. USA 68:2417 (1971). The primary structure of its precursor, pre-pro-NGF, has been deduced from the nucleotide sequence of the mouse NGF cDNA (Scott et al. Nature 302:538 (1983); Ullrich et al. Nature 303:821 (1983)).

The homologous human NGF (hNGF) gene has also been identified (Ullrich, Symp. on Quan. Biol., Cold Spring Harbor 48:435 (1983); U.S. Pat. No. 5,288,622, issued Feb. 22, 1994, which is incorporated herein by reference). Its homology to the mouse NGF is about 90% and 87%, on the amino acid and nucleotide sequence levels, respectively. Due to the scarcity of naturally-occurring human NGF, it has not been prepared from natural sources in quantities sufficient to biochemically characterize in fine detail.

Additional neurotrophic factors related to NGF have since been identified. These include brain-derived neurotrophic factor (BDNF) (Leibrock, et al., Nature, 341:149–152 (1989)), neurotrophin-3 (NT-3) (Kaisho, et al., FEBS Lett., 266:187 (1990); Maisonpierre, et al., Science, 247:1446 (1990); Rosenthal, et al., Neuron, 4:767 (1990)), and neurotrophin 4/5 (NT-4/5) (Berkmeier, et al., Neuron, 7:857–866 (1991)). GDNF, a distant member of the TGF-beta. super family, and neurturin ("NTN") are two, recently identified, structurally related, potent survival factors for sympathetic sensory and central nervous system neurons (Lin et al. Science 260:1130–1132 (1993); Henderson et al. Science 266:1062–1064 (1994); Buj-Bello et al., Neuron 15:821–828 (1995); Kotzbauer et al. Nature 384:467–470 (1996)).

Producing recombinant protein involves transfecting host cells with DNA encoding the protein and growing the cells under conditions favoring expression of the recombinant protein. The prokaryote *E. coli* is has been a favored host because it can be made to produce recombinant proteins in high yields at low cost. Numerous U.S. patents on general bacterial expression of DNA encoding proteins exist, including U.S. Pat. No. 4,565,785 on a recombinant DNA molecule comprising a bacterial gene for an extracellular or periplasmic carrier protein and non-bacterial gene; U.S. Pat. No. 4,673,641 on co-production of a foreign polypeptide with an aggregate-forming polypeptide; U.S. Pat. No. 4,738,921 on an expression vector with a trp promoter/operator and trp LE fusion with a polypeptide such as IGF-I; U.S. Pat. No. 4,795,706 on expression control sequences to include with a foreign protein; and U.S. Pat. No. 4,710,473 on specific circular DNA plasmids such as those encoding IGF-I.

Genetically engineered bio-pharmaceuticals are typically purified from a supernatant containing a variety of diverse host cell contaminants. NGF, in particular, has been reportedly purified to varying extent with varying degrees of effort and success using a number of different methods. See for example, Longo et al., IBRO Handbook, vol. 12, pp 3–30 (1989); U.S. Pat. No. 5,082,774, which discloses CHO cell production of NGF; Bruce and Heinrich (Neurobio. Aging 10:89–94 (1989)); Schmelzer et al. J Neurochem. 59:1675–1683(1992); Burton et al., J Neurochem. 59:1937–1945(1992)). These efforts have been primarily at laboratory scale.

However, preparative isolation of recombinant human NGF resulting in pharmaceutical purity and high yield, essentially free of variants, has eluded the art.

Accordingly, there is a need in the art for an efficient protocol for selectively separating neurotrophins, particularly NGF and NGF-family of neurotrophins, from their variants and other molecules, and from other polypeptides with high pI. The process of purifying neurotrophins at large scale should be applicable to starting material from varying sources, including fermentation broth, lysed bacterial or mammalian cells, to supply clinical needs. Furthermore, as the present inventors have discovered previously unknown, difficult-to-separate neurotrophin variants, for example NGF variants, the methods presented herein are particularly useful to provide commercially useful amounts of recombinant neurotrophins, including human NGF (rhNGF), rhNT-3, and rhNT-4/5 and desirable genetically engineered mutants thereof, that are substantially free of undesirable variants. These and other objects of the invention will now be apparent to one of ordinary skill in the art.

SUMMARY OF THE INVENTION

In one embodiment of the invention a process for purifying a neurotrophin, particularly one in the NGF-family, including NGF, NT-3, NT-4/5, and BDNF which share recognition by a highly homologous family of receptors (trks), preferably rhNGF, rNT-3, rhNT-4/5, rhBDNF or desirable genetically engineered forms thereof, by the use of hydrophobic interaction chromatography (HIC) is provided. In view of the discovery by the present inventors of certain undesirable neurotrophin variants arising from recombinant production of a neurotrophin, as reported herein, the use of HIC can separate chemically different or even misfolded forms of a neurotrophin from the desired correctly folded, intact neurotrophin. Variants that can be removed are those that differ from the mature, correctly folded neurotrophin in hydrophobicity, including partially processed precursor sequences, glycosylated mature and precursor-containing forms (when present from eukaryotic cell culture), and misfolded and partially folded variants (generally from bacterial cell culture when in vitro folding steps are used). For example, HIC is particularly useful to remove partially processed precursor sequences of NGF, glycosylated species of NGF and precursor (when present from eukaryotic cell culture), and misfolded and partially folded variants (generally from bacterial cell culture and in vitro folding steps) from mixtures of mature NGF. NGF has one N-linked glycosylation site at Asn45. In the case of bacteria-expressed, refolded rhNT-4/5, HIC separates correctly folded NT-4/5 from incorrectly folded forms. As a result of the process described herein the neurotrophin is essentially free of these variants. For neurotrophin purification, preferably the HIC resin functional group is a phenyl group, while octyl and butyl groups can be useful. Particularly preferred embodiments include HIC resins Phenyl Toyopearl, Phenyl Sepharose Fast Flow Low Substitution, TSK-Phenyl 5PW, or the like.

In another embodiment is provided a process for purifying a neurotrophin, particularly one in the NGF-family, preferably rhNGF, rNT-3, rhNT-4/5 or desirable genetically engineered forms thereof, by the use of preparative cation-exchange chromatography, which separates charge-modified variants, such as oxidized, isoasp and deamidated forms from mature neurotrophin. Particularly preferred embodiments use SP-Sepharose High Performance, Fractogel EMD SO3, or polyaspartic acid resin, of which PolyCAT A is particularly preferred. Most preferably at large scale SP-Sepharose High Performance or Fractogel EMD SO3 resins are used.

In yet another embodiment of the invention both HIC and cation-exchange chromatography are used to prepare a composition of a desired neurotrophin, for example recombinant mature NGF, preferably human NGF, that is substantially homogenous, i.e., substantially free of both process and charge variants, e.g. misfolded and chemical variants, and is also substantially pure with regard to protein content.

In one embodiment of this invention an improved process for separating neurotrophins, particularly those of the NGF-family, preferably recombinant human NGF, NT-3, NT-4/5, and their desirable genetically engineered forms, from related undesirable variants, e.g. fermentation, protease-cleaved variants, glycosylation variants, misfolded variants, by means of reversed-phase liquid chromatography is provided. More preferably the NGF is the 120/120 or 118/118 homodimer form. As a result of the process described herein the neurotrophin is most preferably essentially free of variants.

In another embodiment a process for purifying neurotrophins, particularly those of the NGF-family, from related variants using elution conditions involving physiological pH is provided.

In still another embodiment a process for purifying a neurotrophin that results in considerable improvement in its homogeneity is provided.

In another embodiment, the invention provides a process for separating NGF-family neurotrophins from variants thereof comprising:

a) loading a buffer containing the neurotrophin and its variant at a pH of about 5 to 8 onto a hydrophobic interaction chromatography column;

b) washing the column c) eluting the neurotrophin with a buffer at a pH of about 5 to 8;

d) loading the neurotrophin-containing eluant onto a cation-exchange chromatography column at a pH from about 5 to 8; and e) eluting the neurotrophin from the column with a buffer at a salt gradient at a pH at about 5 to 8, preferably pH 6. The neurotrophin is most preferably rhNGF.

In one embodiment of the invention is provided a silica gel chromatography step that efficiently removes host cell proteins from the neurotrophin fraction, which is preferably an NGF fraction.

In one embodiment of the invention, a process step is provided in which 120 amino acid NGF is subjected to trypsin-like protease treatment to selectively remove the terminal RA dipeptide from the VRRA C-terminal, to yield the 118 species. An immobilized trypsin column is preferred.

The invention also relates to the neurotrophin composition and formulation prepared by the processes of the invention and to uses for the composition and formulation. Provided is a composition of neurotrophin that is substantially homogenous, i.e., substantially free of both process and charge variants, e.g. misfolded and chemical variants, and is also substantially pure with regard to protein content. Preferably, mature human NGF, mature human or rat NT-3, and mature human NT-4/5 are provided in this form. In a preferred embodiment the NGF is the 120 species, and more preferably the 118 form, most preferably as a homodimer, e.g., 118/118.

BRIEF DESCRIPTION OF THE DRAWINGS

FIG. 1 depicts an SP-Sepharose HP chromatogram. An NGF-containing mixture from a 12 kL fermentation, after HIC chromatography, was loaded onto a SP-Sepharose High Performance resin (column dimension 1.0×35 cm; a 27.5 ml bed volume) of 25 omnifit SPSHP resin. Buffer A was 0.2 M NaCl, 20 mM succinate, pH 6.0 (23 ms). Buffer B was 0.7M NaCl, 20 mM Succinate, pH 6.0 (63 ms). The column was first equilibrated in Buffer A. The HIC pool of 345 ml at 0.24 mg/ml was adjusted to 25 mM succinate, pH 6.0 (17 ms) of which 362 ml was loaded giving a 3 mg/ml resin load; 82.5 mg NGF was loaded. Load rate was 40 cm per hour. NGF was eluted using a 22 column volume gradient from 30% to 80% Buffer B (0.35 to 0.60 M NaCl; 37 to 57 ms). Elution rate was 60 cm per hour. Absorbance units (280 nm) and mS/cm were plotted versus fraction numbers and elution volume in ml. Fractions containing NGF were determined and pooled. In this case fractions 43 to 60 were pooled to obtain 99 ml sample at 0.38 mg/ml NGF, giving about a 46% recovery.

FIG. 2 depicts an SP-NPR HPLC cation-exchange (HPIEX) analysis of the Phenyl Sepharose Fast Flow pool and the SP-Sepharose HP pool. Chromatogram for each are marked.

FIG. 3 depicts an C4 RP-HPLC analysis of selected fractions (main pool, leading edge and trailing edge of main peak pool) from the SP-Sepharose HP chromatography step. The three signals are overlaid and are as marked. As can be seen, the main peak (containing mature NGF) is separated from several lesser peaks that contain variant NGFs.

FIG. 4 depicts the sequence of human prepro-NGF (SEQ ID NO: 1). Indicated on the figure is the first amino acid of mature NGF (position 1) and the last amino acid of the 120 NGF form (position 120). A preferred NGF amino acid sequence is that of the mature 118 form (from position 1 to position 118). Also shown are variant forms: mature 120 (position 1 to position 120); mature 117 (position 1 to 117); R120 (position −1 to 120); and sites for other misprocessing that occurs at the N- and C-terminal ends, including mature 114 (amino acids 1 to 114), 115 (amino acids 1 to 115) and 117 (amino acids 1 to 117) variants. A major misprocessed variant, proteolytically misprocessed, has N-terminal cleavage between amino acids R(−39) and S(−38) in the pro sequence of NGF. The likely initiation Met are underlined. Other N-terminal variants include truncated forms of NGF, with the most common having cleavage occurring between amino acids H8 and R9 and between R9 and G10.

FIG. 5 depicts the amino acid sequences of neurotrophins human NGF (SEQ ID NO: 2), mouse NGF (SEQ ID NO: 3), BDNF (SEQ ID NO: 4), NT-3 (SEQ ID NO: 5) and NT-4/5 (SEQ ID NO: 6). The 15 boxed regions indicate the homologous cysteine-containing regions involved in the cysteine knot motif (De Young et al., Protein Sci. 5 (8): 1554–66 (1996)).

FIG. 6 depicts the chromatography pattern of rhNT-4/5 on DEAE-Sepharose Fast Flow (DEFF) resin column. The chromatogram marked "NT45DE1:1_UV" is a UV absorbance measurement at 280 mn. The chromatogram marked "NT45DE1:1_Cond1" is a conductivity measurement of eluting fractions. The neurotrophin-containing fractions that were pooled are indicated by the horizontal arrow marked "Pool."

FIG. 7 depicts the chromatography pattern of rhNT-4/5 on SP-Sepharose Fast Flow resin column. The chromatogram marked "NT45SFF1:1_V" is a UV absorbance measurement at 280 nm. The chromatogram marked "NT45SFF1:1_Cond1" is a conductivity measurement of eluting fractions. The neurotrophin-containing fractions that were pooled are indicated by the horizontal arrow marked "Pool."

FIG. 8 depicts a typical preparative C4-RP-HPLC chromatography pattern of rhNT-4/5 under conditions described in the text. Absorbance at 280 nm was monitored. The neurotrophin-containing fractions that were pooled are marked with a horizontal arrow marked "Pool."

FIG. 9 provides the analytical HPLC chromatography pattern of NT4/5 samples monitored during refolding at the times indicated. Column conditions are described in the text. "NT-4/5 Std." indicates the elution pattern of a correctly folded, intact NT-4/5 used as a standard. The pattern marked "SSFF (0.5 m)" depicts the analysis of NT-4/5 eluted with 0.5M NaCl from the S-Sepharose Fast Flow column prior to refolding. As NT-4/5 refolds, the elution pattern approaches that of the standard.

FIG. 10 depicts a chromatogram showing separation of intact, correctly folded NT-4/5 from misfolded variants on a hydrophobic interaction chromatography column, Phenyl Toyopearl 650M column. Misfolded variants that are less hydrophobic than correctly folded NT-4/5 elute in the flow-through, while misfolded variants (Peak B) that are more hydrophobic elute at an organic solvent concentration higher than that needed to elute correctly folded NT-4/5 (Peak A).

FIG. 11 depicts the elution pattern of NT-4/5 and variants from a cation exchange resin, SP-Sepharose. Absorbance at 280 nm was monitored. Peak A contains carbamylated and clipped variants, hile Peak B contains intact, correctly folded NT-4/5. NT-4/5-containing fractions that were pooled are indicted by the horizontal arrow marked "Pool."

FIG. 12 depicts a typical preparative poly CAT A resin chromatography pattern of rhNT-4/5 under conditions described in the text.

FIG. 13 depicts a 16% SDS-PAGE (Tris-glycine system, pre-poured, from Novex, Inc., San Diego, Calif.) analysis under reducing conditions to assess purity and homogeneity of samples taken from the indicated steps of the rhNT4/5 purification process described in the text. The gel was stained with Coomassie-R250 to detect protein (Andrews, Electrophoresis, Oxford University Press: New York, 1986). The lane marked "DE Load" contains a sample of the PEI-mixture that was loaded onto the DE-Sepharose Fast Flow column; lane marked "DE FT" contains a sample of the flow through from the DE-Sepharose Fast Flow column; lane "S Pool" contains a sample from the pooled fractions containing NT-4/5 eluted from the S-Sepharose Fast Flow resin column, prior to refolding; lane "Refold Pool" contains a sample of the pool after refolding was completed; lane "C4 Pool" contains a sample of the pooled fractions after preparative C4 RP-HPLC; and lane "PolyCAT A Pool" contains a sample from the pooled NT-4/5-fractions from the Poly-CAT A HPLC column.

FIG. 14 depicts the UV absorbance pattern of fractions from S-Sepharose Fast Flow chromatography of a mixture containing bacterially-produced, sulfonylated rhNT-3.

FIG. 15 depicts Macroprep High S cation-exchange chromatography of a mixture containing in vitro re-folded forms of rhNT-3. The resin was purchased from Biorad. Column dimensions were 9×9 cm. A 700 ml SSFF pool containing refolded (after 36 hour refold), pH 6.8, was loaded onto the Macroprep column at a flow of about 310 ml/min. Conditions are given in the text.

FIG. 16 depicts a Phenyl Sepharose Fast Flow High Substitution (hydrophobic interaction chromatography) chromatography of cation-exchange-purified, refolded rhNT-3 to remove misfolded variants.

FIG. 17 depicts a SP-Sepharose High Performance chromatography of the HIC-rhNT-3 pool.

DETAILED DESCRIPTION OF THE PREFERRED EMBODIMENT

Definitions

As used herein, "neurotrophin" refers to a neurotrophin, preferably an NGF-family neurotrophin, including NGF, NT-3, NT-4/5, and BDNF, from any species, including murine, bovine, ovine, porcine, equine, avian, and preferably human, in native sequence or in a genetically engineered form, and from any source, whether natural, synthetic, or recombinantly produced. For example, "NGF" refers to nerve growth factor from any species, including murine, bovine, ovine, porcine, equine, avian, and preferably human, in native sequence or in genetically engineered variant form, and from any source, whether natural, synthetic, or recombinantly produced. Preferably, the neurotrophin is recombinantly produced. In a preferred method, the neurotrophin is cloned and its DNA expressed, e.g., in mammalian cells, in bacterial cells. The processes and methods taught herein can also be applied to the neurotrophins GDNF and neurturin.

Preferred for human use is human native-sequence, mature NGF, more preferably a 120 amino acid sequence, and even more preferably a 118 amino acid sequence. More preferably, this native-sequence NGF is recombinantly produced. The preferred amino acid sequence for human pre-pro-NGF and human mature NGF are provided by U.S. Pat. No. 5,288,622, which is specifically incorporated herein by reference. The 120 amino acid form, without additional post-translational modifications, is a preferred form in the homodimer form (i.e., 120/120). Even more preferred is the 118 form, without additional post-translational modifications, particularly as a homodimer (i.e., 118/118).

By "substantially pure" is meant a degree of purity of total neurotrophin, e.g., NGF, to total protein where there is at least 70% neurotrophin, more preferably at least 80%, and even more preferably increasing to at least 90%, 95% or 99%. A particularly preferred purity is at least 95%. By "essentially pure" is meant that the composition is at least 90% or more pure for the desired neurotrophin.

By "substantially free of neurotrophin variant" is meant a composition in which the percent of desired neurotrophin species to total neurotrophin (including less desirable neurotrophin species) is at least 70% desired neurotrophin species, more preferably at least 80%, and even more preferably increasing to at least 90%, 93%, 95% or 99%. By "essentially free" is meant that the composition contains at least 90% or more desired neurotrophin. A particularly preferred level is at least 95% desired neurotrophin e.g., correctly folded, intact 118/118 rhNGF, species. The other undesirable species or forms may be misprocessed forms or chemical variants, e.g. altered charge variants, resulting from the fermentation or purification process, or preferably all of the foregoing, as disclosed herein. For example, when NGF is folded in vitro after synthesis in bacteria, "species" or "variants" can include misfolded or partially folded forms.

By "misfolded" variant is meant a variant of the neurotrophin which differs from the neurotrophin by the pairing of its cysteine residues or by the particular cysteine residues which are free or blocked. Misfolded variants can also have the same cysteine pairing as the neurotrophin but have a different three dimensional conformation resulting from misfolding.

By "chemical" variant is meant a variant that differs chemically from the neurotrophin, for example by having an altered charge, by carbamylation, deamidation, oxidation, glycosylation, or proteolytic cleavage.

Buffers for the column aspect of this invention generally have a pH in the range of about 5 to 8. Buffers that will control the pH within this range include, for example, citrate, succinate, phosphate, MES, ADA, BIS-TRIS Propane, PIPES, ACES, imidazole, diethylmalonic acid, MOPS, MOPSO, TES, TRIS buffer such as TRIS-HCl, HEPES, HEPPS, TRICINE, glycine amide, BICINE, glycylglycine, and borate buffers. A preferred buffer is a MOPSO buffer.

As used herein, "alcohols" and "alcoholic solvents" are meant in the sense of the commonly used terminology for alcohol, preferably alcohols with 1 to 10 carbon atoms, more preferably methanol, ethanol, iso-propanol, n-propanol, or t-butanol, as well as glycerol, propylene glycol, ethylene glycol, hexylene glycol, polypropylene glycol, and polyethylene glycol, and most preferably ethanol or iso-propanol. Such alcohols are solvents that, when added to aqueous solution, increase the hydrophobicity of the solution by decreasing solution polarity.

MOPSO is 3-(N-Morpholino)-2-hydroxypropanesulfonic acid. HEPES is N-2-Hydroxyethylpiperazine-N'-2-ethanesulfonic acid. Reagent alcohol is 95 parts by volume (Specially Denatured Alcohol Formula 3A and 5 parts by volume isopropyl alcohol). MES is 2-(N-Morpholino) ethanesulfonic acid. UF/DF means ultrafiltration/diafiltration. TMAC is tetramethylammonium chloride. TEAC is tetraethylammonium chloride. NGF-120 means full-length of 120/120 nerve growth factor. NGF-118 means homodimeric mature NGF molecule of 118 residues. Oxidized NGF means NGF variant molecule, Metsulfoxide$_{37}$, which is reported herein to be about 80% as biologically active as mature, native NGF. Isoasp NGF means NGF isomerized variant molecule, Asp93. Deamidated NGF means NGF having Asn45 converted to Asp45. RNGF means an NGF molecule with an extra Arginine residue at its N-terminus. CHO means Chinese hamster ovary cells.

Resins described herein include MACROPREP HIGH S Cation-exchange (BIO-RAD Laboratories; strong cation exchange; $SO_3$ functional group; nominal particle size of 50 m; nominal pore size of 1000 A); Silica gel (underivatized); Phenyl Sepharose Fast Flow Low Substitution (Pharmacia; highly cross-linked 6% agarose; particle size of 45–165 microns); SP-Sepharose HP (Pharmacia; highly cross-linked 6% agarose; particle size of 34 microns); Phenyl Toyopearl 650 M (TosoHaas; particle size of 40–90 microns); and Fractogel EMD $SO_3$—650 S (EM Separations, a U.S. associate of E. Merck (Germany); particle size of 25–40 m).

Modes for Carrying out the Invention

Neurotrophins belong to a family of small, basic proteins which play a crucial role in the development and maintenance of the nervous system. The first identified and probably best understood member of this family is nerve growth factor (NGF). See U.S. Pat. No. 5,169,762, issued Dec. 8, 1992. Recently, sequentially related but distinct polypeptides with similar functions to NGF have been identified. For example, brain-derived neurotrophic factor (BDNF), also referred to as neurotrophin-2 (NT2), was cloned and sequenced by Leibrock et al.(Nature, 341: 49–152 [1989]). Several groups identified a neurotrophic factor originally called neuronal factor (NF), and now referred to as neurotrophin-3 (NT3). (Emfors et al., Proc. NatL. Acad. Sci. USA, 87:5454–5458 [1990]; Hohn et al., Nature, 344:339 [1990]; Maisonpierre et al., Science, 247:1446 [1990]; Rosenthal et al., Neuron, 4:767 [1990]; Jones and Reichardt, Proc. Natl. Acad. Sci. USA, 87:8060–8064 [1990]; Kaisho et al., FEBS Lett., 266:187 [1990]). Neurotrophin-4/5 (referred to as either NT4 or NT5) has been identified (Hallbook et al., Neuron, 6:845–858 [1991]; Berkmeier et al., Neuron, 7:857–866 [1991]; Ip et al., Proc. Natl. Acad. Sci, USA, 89: 3060–3064 [1992]). U.S. Pat. No. 5,364,769, issued Nov. 15, 1994, discloses human NT-4/5 and processes for its recombinant expression and is incorporated herein by reference. Also reported are chimeric and pantropic neurotrophins, such as that reported in U.S. Pat. No. 5,488,099, issued Jan. 30, 1996, in Urfer et al., EMBO J 13(24): 5896–909 (1994), and in WO 95/33829, published Dec. 1, 1995 (incorporated herein by reference) in which the neurotrophin has been modified to bind to more than one receptor or contains a receptor binding activity not normally present to a significant degree in the native neurotrophin. Of particular interest are neurotrophins designated MNTS-1 and D15A NT3. Also of particular interest are neurotrophins having an NGF amino acid backbone but modified to bind receptors other than trkA, such as trkB or trkC. Preferred are those in which amino acid substitutions have been made in NGF with an amino acid from a corresponding position in NT-3 that is responsible for binding the trk receptor for NT-3. Such NGF mutants have NT-3-like receptor binding activity while retaining NGF pharmacokinetics and purification behavior (Urfer, et al, Biochemistry 36(16): 4775–4781 (1997)). These NGF mutants can also lack trkA binding activity (Shih et al, J Biol. Chem. 269 (44): 27679–86 (1994). Such NGF mutants are particularly preferred neurotrophins for use in the invention described herein.

The isolation of a recombinant human neurotrophin, e.g., rhNGF, involves separation of the protein from a variety of diverse host cell contaminants. Each step involves special buffers that enable sufficient separation to take place. The final or penultimate processing step for a neurotrophin is complicated by the presence of several neurotrophin variants that co-purify using conventional chromatographic media. When a refolding step is included in the recovery and purification process, the variants include misfolded forms of the neurotrophin. Variants can also include those that differ chemically from the neurotrophin, such as carbamylated, deamidated, deamidated or proteolytically cleaved forms. In the case of NGF, these species consist primarily of dimeric forms—homodimers, e.g., 120/120 or 117/117 when 118/118 is desired, or heterodimers, e.g., 120/118, 117/118—, chemically modified variants—isoaspartate, mono-oxidized, glycosylation variants, N-terminal and C-terminal truncated forms, and dimers thereof.

The invention makes possible the large scale production of neurotrophins, particularly rhNGF, in quantities sufficient for therapeutic uses, such as, for example, treatment of Alzheimer's disease, peripheral neuropathies, including diabetic and AIDS-related neuropathies, and the like.

In view of the similarity in sequence and conformation between NGF and other neurotrophins, preferably those in the NGF-family, the methods of the present invention can be applied to prepare these neurotrophins substantially free of misprocessed, misfolded or partially folded, glycosylation, and/or charge variants. In the present invention, column resins and conditions are identified that are favorable for selectively separating neurotrophins from these and other closely related variants. Neurotrophins include NT-3, NT-4/5, NT-6, BDNF, and engineered forms, including heterodimeric, chimeric or pantropic forms thereof. Preferably the neurotrophins are-human or highly homologous to the human amino acid sequence, preferably greater than 80%, more preferably greater than 90%, and most preferably greater than 95% homologous to the human sequences. An engineered neurotrophin will retain at least 50% of the trk receptor binding function of the native neurotrophin it mimics, preferably at least 75%, and more preferably at least 80%. These engineered forms are those that retain sufficient high-pI or hydrophobic character of the native neurotrophin to retain a similar performance in the processes described herein.

As described below, the processes described herein have been successfully applied to rhNGF, rhNT-3 and rhNT-4/5. For example, rhNT-4/5, which was made in *E. coli*, was isolated in inclusion bodies and reduced and solubilized from the inclusion bodies. The reduced NT-4/5 was partially purified by DE. Sepharose Fast Flow and by S-Sepharose Fast Flow chromatography. The S-Sepharose Fast Flow pool was refolded in a guanidine containing buffer for 24 hours. Misfolded forms of NT-4/5 were removed by chromatography as disclosed herein at large scale. The carbamylated and clipped (misprocessed forms) of NT-4/5 were removed by high performance cation-exchange chromatography by a PolyCat A HPLC resin or SP-Sepharose HP resin, in column format, at large scale. The purified rhNT-4/5 was ultrafiltered and diafiltered into an acidic buffer for formulation.

One embodiment of the invention involves purifying a neurotrophin from its related variants, usually after the neurotrophin has already been purified from most other impurities, typically at the final or near final step before desalting or diafiltration prior to formulation. The related variants in the mixture can include not only variants residual from a fermentation, but also variants produced if the neurotrophin is degraded on storage or during processing.

The neurotrophins suitable for use with embodiments of the invention can be prepared by any means, but are preferably prepared recombinantly. A nucleic acid molecule coding for the neurotrophins discussed herein are available from several sources, for example, through chemical synthesis using the known DNA sequence or by the use of standard cloning techniques known to those skilled in the art. cDNA clones carrying the neurotrophin, e.g., hNGF coding sequence, can be identified by use of oligonucleotide hybridization probes specifically designed based on the known sequence of the neurotrophin.

Upon obtaining a molecule having the neurotrophin coding sequence, the molecule is inserted into a cloning vector appropriate for expression in the chosen host cell. The cloning vector is constructed so as to provide the appropriate regulatory functions required for the efficient transcription, translation and processing of the coding sequence.

If the neurotrophin is prepared recombinantly, suitable host cells for expressing the DNA encoding the neurotrophin are prokaryote, yeast, or higher eukaryotic cells. Suitable prokaryotes for this purpose include bacteria such as archaebacteria and eubacteria. Preferred bacteria are eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans,* and *Shigella*; Bacilli such as *B. subtilis* and *B. licheniformis* (e.g., *B. licheniformis* 41P disclosed in DD 266,710 published Apr. 12, 1989); *Pseudomonas* such as *P. aeruginosa; Streptomyces; Azotobacter; Rhizobia; Vitreoscilla;* and *Paracoccus*. Suitable *E. coli* hosts include *E. coli* W3110 (ATCC 27,325), *E. coli* 94 (ATCC 31,446), *E. coli* B, and *E. coli* X1776 (ATCC 31,537). These examples are illustrative rather than limiting.

Incorporated herein in its entirety is PCT publication WO 95/30686 published Nov. 16, 1995. The publication is particularly relevant for its description of bacterial synthesis and in vitro folding of NGF. The products from that process can be subjected to the purification methods of the present invention.

Mutant cells of any of the above-mentioned bacteria may also be employed. It is, of course, necessary to select the appropriate bacteria taking into consideration replicability of the replicon in the cells of a bacterium. For example, *E. coli, Serratia,* or *Salmonella* species can be suitably used as the host when well known plasmids such as pBR322, pBR325, pACYA177, or pKN410 are used to supply the replicon. *E. coli* strain W3110 is a preferred host or parent host because it is a common host strain for recombinant DNA product fermentation. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonAΔ; *E. coli* W3110 strain 9E4, which has the complete genotype tonAΔptr3; *E. coli* W3110 strain 27C7 (ATCC 55,244), which has the complete genotype tonA ptr3 phoAΔE15 Δ (argF-lac) 169ΔdegPΔompT kan<r>; *E. coli* W3110 strain 37D6, which has the complete genotype tonA ptr3 phoA Δ E15 Δ (argF-lac)169 Δ degP Δ ompT Δ rbs7 ilvG kan r; *E. coli* W3110 strain 40 B4, which is strain 37D6 with a non-kanamycin resistant degP deletion mutation; and an *E. coli* strain having mutant periplasmic protease disclosed in U.S. Pat. No. 4,946,783 issued Aug. 7, 1990.

Human NGF has been expressed in *E. coli*. The isolation and sequence of the gene encoding the .beta.-subunit of hNGF and its expression as a heterologous protein in *E. coli* was described in U.S. Pat. No. 5,288,622. The teachings therein are also suitable to provide mammalian cell produced mature human NGF. By using recombinant techniques, human .beta.-NGF was expressed free from other mammalian proteins. Expression of the hNGF in *E. coli* using two genes which contain altered amino-termini resulted in the expression of a fused protein, which was described by Iwai et al., Chem. Pharm. Bull. 34:4724(1986).

In addition to prokaryotes, eukaryotic microbes such as filamentous fungi or yeast are suitable expression hosts for neurotrophin-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe* [Beach and Nurse, Nature, 290: 140 (1981); EP 139,383 published May 2, 1985]; *Kluyveromyces* hosts [U.S. Pat. No. 4,943,529; Fleer et al., Bio/Technology, 9: 968–975 (1991)] such as, e.g., *K. lactis* [MW98–8C, CBS683, CBS4574; Louvencourt et al., *J. Bacteriol.*, 737 (1983)], *K. fragilis* (ATCC 12,424), *K. bulgaricus* (ATCC 16,045), *K. wickeramii* (ATCC 24,178), *K. waltii* (ATCC 56,500), *K. drosophilarum* [ATCC 36,906; Van den Berg et al., Bio/Technology, 8: 135 (1990)], *K. thermotolerans,* and *K. marxianus; yarrowia* [EP 402,226]; *Pichia pastoris* [EP 183,070; Sreekrishna et al., J. Basic Microbiol., 28: 265–278 (1988)]; *Candida; Trichoderma reesia* [EP 244,234]; *Neurospora crassa* [Case et al., Proc. Natl. Acad. Sci. USA, 76: 5259–5263 (1979)]; *Schwanniomyces* such as *Schwanniomyces occidentalis* [EP 394,538 published Oct. 31, 1990]; and filamentous fungi such as, e.g., *Neurospora, Penicillium, Tolypocladium* [WO 91/00357 published Jan. 10, 1991], and *Aspergillus* hosts such as *A. nidulans* [Ballance et al., Biochem. Biophys. Res. Commun., 112: 284–289(1983); Tilbum et al., Gene, 26: 205–221 (1983); Yelton et al., Proc. Natl. Acad. Sci. USA, 81: 1470–1474 (1984)] and *A. niger* [Kelly an Hynes, EMBO J., 4: 475–479 (1985)].

Suitable host cells appropriate for the expression of the DNA encoding the neurotrophin can also be derived from multicellular organisms. Such host cells are capable of complex processing and glycosylation activities. In principle, any higher eukaryotic cell culture is suitable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow el al., Bio/Technology, 6:47–55 (1988); Miller et al., in Genetic Engineering, Setlow, J. K. et al., eds., Vol. 8 (Plenum Publishing, 1986), pp; 277–279; and Maeda et al., Nature, 315: 592–594 (1985). A variety of viral strains for transfection are publicly available, e.g., the L-1 variant of *Autographa californica* NPV and the Bm-5 strain of *Bombyx mori* NPV, and such viruses may be used herein, particularly for transfection of *Spodoptera frugiperda* cells. Human NGF has been produced in insect cells as reported in U.S. Pat. No. 5,272,063, issued Dec. 21, 1993.

Plant cell cultures of cotton, corn, potato, soybean, petunia, tomato, and tobacco can be utilized as hosts. Typically, plant cells are transfected by incubation with certain strains of the bacterium *Agrobacterium tumefaciens,* which have been previously manipulated to contain the DNA encoding the neurotrophin. During incubation of the plant cell culture with *A. tumefaciens,* the DNA encoding the neurotrophin is transferred to the plant cell host such that it is transfected, and will, under appropriate conditions, express the DNA encoding the neurotrophin. In addition, regulatory and signal sequences compatible with plant cells are available, such as the nopaline synthase promoter and polyadenylation signal sequences (Depicker et al, J. Mol. Appl. Gen., 1:561 (1982)). In addition, DNA segments isolated from the upstream region of the T-DNA 780 gene are capable of activating or increasing transcription levels of plant-expressible genes in recombinant DNA-containing plant tissue (EP 321,196 published Jun. 21, 1989).

Examples of useful mammalian host cell lines are monkey kidney CVI line transformed by SV40 (COS-7, ATCC CRL 1651); human embryonic kidney line [293 or 293 cells subcloned for growth in suspension culture, Graham et al., J. Gen Virol., 36: 59 (1977)]; baby hamster kidney cells (BHK, ATCC CCL 10); Chinese hamster ovary cells/-DHFR [CHO, Urlaub and Chasin, Proc. Natl. Acad Sci. USA, 77: 4216 (1980)]; mouse sertoli cells [TM4, Mather, Biol. Reprod., 23: 243–251 (1980)]; monkey kidney cells (CV1, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells [Mather et al., Annals N.Y. Acad. Sci., 383: 44–68 (1982)]; MRC 5 cells; FS4 cells;-and a human hepatoma line (Hep G2). A preferred method is expression in CHO cells. The exon of human NGF containing the prepro-NGF can be used to achieve expression of secreted, mature NGF (including 118 and 120 forms) using suitable promoters and vectors (U.S. Pat. No. 5,288, 622). Cultures of stable CHO cells stably transfected and secreting mature forms of NGF are useful in the invention as discussed in the Examples herein.

Host cells are transfected and preferably transformed with the above-described expression or cloning vectors and cultured in conventional nutrient media modified as appropriate for inducing promoters, -selecting transformants, or amplifying the genes encoding the desired sequences. Transfection refers to the taking up of an expression vector by a host cell whether or not any coding sequences are in fact expressed. Numerous methods of transfection are known to the ordinarily skilled artisan, for example, CaPO4 and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., Molecular Cloning: A Laboratory Manual [New York: Cold Spring Harbor Laboratory Press, 1989], or electroporation is generally used for prokaryotes or other cells that contain substantial cell-wall barriers. Infection with Agrobacterium tumefaciens is used for transformation of certain plant cells, as described by Shaw et al., Gene, 23:315 (1983) and WO 89/05859 published Jun. 29, 1989. In addition, plants may be transformed using ultrasound treatment as described in WO 91/00358 published Jan. 10, 1991.

For mammalian cells without such cell walls, the calcium phosphate precipitation method of Graham and van der Eb, Virology, 52: 456–457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen et al, J Bact., 130: 946 (1977) and Hsiao et al., Proc. Natl. Acad. Sci. (USA), 76: 3829 (1979). However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., Methods in Enzymology (1990) Vol. 185, pp. 527–537, and Mansour et al., Nature, 336: 348–352 (1988).

Preferably, the gene for hNGF is inserted into the vector so as to have available a methionine initiation codon, preferably one of the two methionine initiation codons as identified by Ullrich et al. (Nature, 303:821–825 (1983)). The hNGF gene (Ullrich, et.al., Cold Spring Harbor Symposia on Quant. Biol. XLVIII, p. 435 (1983); U.S. Pat. No. 5,288,622) has two nearly adjacent methionines that are likely to be utilized as translational initiation codons (position 1 refers to the N-terminal serine residue of mature hNGF). In contrast, the mouse submaxillary gland cDNA for NGF, the most thoroughly studied of the nerve growth factors, has a methionine at position −187 in addition to those at positions −121 and −119. In a preferred embodiment for expression in mammalian cells, the prepro-NGF sequence is present.

If prokaryotic cells are used to produce neurotrophin, they are cultured in suitable media in which the promoter can be constitutively or artificially induced as described generally, e.g., in Sambrook et al., Molecular Cloning: A Laboratory Manual (Cold Spring Harbor Laboratory Press, New York 1989). Any necessary supplements besides carbon, nitrogen, and inorganic phosphate sources can also be included at appropriate concentrations introduced alone or as a mixture with another supplement or medium such as a complex nitrogen source.

If mammalian host cells are used to produce neurotrophin, they may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, Meth. Enz., 58: 44 (1979); Barnes and Sato, Anal. Biochem., 102:255 (1980); U.S. Pat. Nos. 4,767,704; 4,657,866; 4,927,762; 5,122,469; or 4,560,655; WO 90/03430; WO 87/00195; or U.S. Pat. No. Re. 30,985, the disclosures of all of which are incorporated herein by reference, can be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin TM drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of in vitro mammalian cell cultures can be found in Mammalian Cell Biotechnology: A Practical Approach, M. Butler, ed. (IRL Press at Oxford University Press, Oxford, 1991). The above process can be employed whether the neurotrophin is produced intracellularly, produced in the periplasmic space, or directly secreted into the medium.

Typically culture fluid is harvested after a suitable period and standard identification assays, for example, immunoassays such as ELISA and Western blot analysis, or biological assays, such as PC12 cell differentiation (Greene, L. A., Trends Neurosci. 7:91 (1986)) are performed. Assays to determine the kind and extent of the variants disclosed herein are known in the art or are provided or cited in the Examples (see, for example, Schmelzer et al. J Neurochem. 59 (5): 1675–83 (1992) and Burton et al., J Neurochem. 59(5):1937–45 (1992), which are incorporated herein by reference.

The neurotrdphin composition prepared from the cells is preferably subjected to at least one purification step prior to HIC. Examples of suitable purification steps include those that are described herein, including affinity chromatography, other techniques for protein purification such as chromatography on silica, chromatography on heparin Sepharose, chromatography on an anion or cation exchange resin (such as a polyaspartic acid column), chromatofocusing, and preparative SDS-PAGE, depending on the neurotrophin to be recovered and starting culture used.

In one embodiment where the neurotrophin is directly secreted into the medium, the medium is separated from the cellular debris by centrifugation, and the clarified fermentation broth or medium is then used for purification on silica gel. For the silica chromatography, typically the broth is passed through underivatized silica particles such that the neurotrophin polypeptide adheres to the silica particles; the silica particles are washed to remove contaminants; and the polypeptide is eluted from the silica particles with a buffer comprising an alcoholic or polar aprotic solvent and an alkaline earth, an alkali metal, or an inorganic ammonium salt.

In a preferred embodiment of the invention, Macroprep High S Cation-Exchange Chromatography is employed to separate neurotrophin from its variants, as well as for decreasing bulk contaminants. This resin can be used as an early step in the purification of a neurotrophin from mammalian cell culture, preferably for fractionation of the harvested cell culture medium. In another embodiment Macroprep High S Cation-Exchange Chromatography is most preferably used immediately after a protein refolding step. The very high flow property of this cation exchange column allows the large volume of dilute refolded protein or harvested cell culture medium neurotrophin to be readily concentrated before subsequent chromatography steps, such as HIC or SP-Sepharose, by adjusting conditions so that the neurotrophins bind the column. Furthermore, the cation exchange nature of the resin allows removal of non-bound bulk proteins and some misprocessed variants and chemically-modified variants (e.g., altered charge, MET37-oxidized variant). Most importantly, when misfolded variants or chemically modified variants (e.g. misprocessed variants, glycosylation variant (as from mammalian cell culture production)) that differ in hydrophobicity from native neurotrophin are present, the Macroprep resin allows at least a partial removal of these hydrophobic variants, substantially enriching for the native neurotrophin, as determined herein. While not meant to be limiting, it is believed that the backbone of the resin support contains hydrophobic content that promotes non-specific interactions between neurotrophins and the resin, which has been taken advantage of as taught herein. Typically, for an elution buffer of pH from about pH 5 to 8, more preferably 6 to 8, a 0 to 3 M TMAC concentration is useful. Sodium acetate, when present to increase the ionic strength of the elution buffer, allows use of lower TMAC concentration. Chloride is a preferred substitute for acetate ion.

In one example of the embodiment where the neurotrophin is produced in the periplasmic space, the culture medium or lysate is centrifuged to remove particulate cell debris. The membrane and soluble protein fractions can then be separated if necessary. The neurotrophin can then be purified from the soluble protein fraction and from the membrane fraction of the culture lysate, depending on whether the neurotrophin is membrane bound, is soluble, or is present in an aggregated form. The neurotrophin thereafter is solubilized and then subsequently refolded using an appropriate buffer. The details for this method of isolation from the periplasm to produce refolded protein are described below.

Insoluble, non-native neurotrophin is isolated from the prokaryotic host cells in a suitable isolation buffer by any appropriate technique, e.g., one involving exposing the cells to a buffer of suitable ionic strength to solubilize most host proteins, but in which aggregated neurotrophin is substantially insoluble, and disrupting the cells so as to release the inclusion bodies and make them available for recovery by, for example, centrifugation. This technique is well known, and is described, for example, in U.S. Pat. No. 4,511,503.

Briefly, the cells are suspended in the buffer (typically at pH 5 to 9, preferably about 6 to 8, using an ionic strength of about 0.01 to 2M, preferably 0.1 to 0.2M). Any suitable salt, including sodium chloride, is useful to maintain a sufficient ionic strength value. The cells, while suspended in this buffer, are then disrupted by lysis using techniques commonly employed such as, for example, mechanical methods, e.g., a Manton-Gaulin press microfluidizer, a French press, or a sonic oscillator, or by chemical or enzymatic methods.

Examples of chemical or enzymatic methods of cell disruption include spheroplasting, which entails the use of lysozyme to lyse the bacterial wall (Neu et al., Biochem. Biophys. Res. Comm., 17:215 (1964)), and osmotic shock, which involves treatment of viable cells with a solution of high tonicity and with a cold-water wash of low tonicity to release the polypeptides (Neu et al., J. Biol. Chem., 240: 3685–3692 (1965)). A third method, described in U.S. Pat. No. 4,680,262, involves contacting the transformed bacterial cells with an effective amount of a lower alkanol having 2 to 4 carbon atoms for a time and at a temperature sufficient to kill and lyse the cells.

After the cells are disrupted, the suspension is typically centrifuged to pellet the inclusion bodies. In one embodiment, this step is carried out at about 500 to 15,000 times g, preferably about 12,000 times g, in a standard centrifuge for a sufficient time that depends on volume and centrifuge design, usually about 10 minutes to 0.5 hours. The resulting pellet contains substantially all of the insoluble polypeptide fraction, but if the cell disruption process is not complete, it may also contain intact cells or broken cell fragments. Completeness of cell disruption can be assayed by resuspending the pellet in a small amount of the same buffer solution and examining the suspension with a phase-contrast microscope. The presence of broken cell fragments or whole cells indicates that additional disruption is necessary to remove the fragments or cells and the associated non-refractile polypeptides. After such further disruption, if required, the suspension is again centrifuged and the pellet recovered, resuspended, and analyzed. The process is repeated until visual examination reveals the absence of broken cell fragments in the pelleted material or until further treatment fails to reduce the size of the resulting pellet.

In an alterriative embodiment, the neurotrophin is isolated from the periplasmic space by solubilization in a suitable buffer. This procedure can be in-situ solubilization involving direct addition of reagents to the fermentation vessel after the neurotrophin has been produced recombinantly, thereby avoiding extra steps of harvesting, homogenization, and centrifugation to obtain the neurotrophin. The remaining particulates can be removed by centrifugation or filtration, or combinations thereof.

If the neurotrophin is being unfolded, the degree of unfolding is suitably determined by chromatography of the non-native neurotrophin, including RP-HPLC. Increasing peak area for the non-native material indicates how much non-native neurotrophin is present.

Once obtained from the solubilized inclusion bodies or at a later stage of purification, the neurotrophin is suitably refolded into an active conformation as described below.

If the neurotrophin is not already in soluble form before it is to be refolded, it may be solubilized by incubation in alkaline buffer containing chaotropic agent and reducing agent in amounts necessary to substantially solubilize the neurotrophin. This incubation takes place under conditions of neurotrophin concentration, incubation time, and incubation temperature that will allow solubilization of the neurotrophin to occur in the alkaline buffer.

Measurement of the degree of solubilization of the neurotrophin in the buffer is suitably carried out by turbidity determination, by analyzing neurotrophin fractionation between the supernatant and pellet after centrifugation on reduced SDS gels, by protein assay (e.g., the Bio-Rad protein assay kit), or by HPLC.

The pH range of the alkaline buffer for solubilization typically is at least about 7.5, with the preferred range being about 8–11. Examples of suitable buffers that will provide a pH within this latter range include glycine, CAPSO (3-[Cyclohexylamino]-2-hydroxy-1-propanesulfonic acid), AMP (2-Amino-2-methyl-1-propanol), CAPS (3-[Cyclohexylamino]-1-propanesulfonic acid), CHES (2-[N-Cyclohexylamino]ethanesulfonic acid), and TRIS HCl (Tris [hydroxymethyl]aminomethane hydrochloride). The preferred buffer herein is glycine or CAPSO, preferably at a concentration of about 20 mM, at a pH of about 8.5 to 11, preferably about 10–11.

The concentration of neurotrophin in the buffered solution for solubilization must be such that the neurotrophin will be substantially solubilized and partially or fully reduced and denatured. Alternatively, the neurotrophin may be initially insoluble. The exact amount to employ will depend, e.g., on the concentrations and types of other ingredients in the buffered solution, particularly the type and amount of reducing agent, the type and amount of chaotropic agent, and the pH of the buffer. For example, the concentration of neurotrophin may be increased at least three-fold if the concentration of reducing agent, e.g., DTT, is concurrently increased, to maintain a ratio of DTT:neurotrophin of from about 3:1 to 10:1. It is desirable to produce a more concentrated solubilized protein solution prior to dilution refolding. Thus, the preferred concentration of neurotrophin is at least about 30 mg/mL, with a more preferred range of 30–50 mg per mL. For example, neurotrophin may be solubilized to a concentration of about 30–50 mg/mL in 5M to 7M urea, 10 mM DTT and diluted, for example, to about 1 mg/mL for folding.

After the neurotrophin is solubilized, it is placed or diluted into a refolding buffer containing 5–40% (v/v) alcoholic or aprotic solvent, a chaotropic agent, and an alkali metal, alkaline earth, or ammonium salt. The buffer can be any buffer for the first buffered solution, with CAPSO, glycine, and CAPS being preferred at pH 8.5–11, particularly at a concentration of about 20 mM, and most preferably CAPSO and glycine. The neurotrophin may be diluted with the refolding buffer, preferably at least five fold, more preferably at least about ten fold. Alternatively, the neurotrophin may be dialyzed against the refolding buffer. The refolding can be carried out at about 2°–45° C., most preferably about 2°–8° C. at least about one hour. The solution optionally also contains a reducing agent and an osmolyte.

The reducing agent is suitably selected from those described above for the solubilizing step in the concentration range given. Its concentration will depend especially on the concentrations of alkaline earth, alkali metal, or ammonium salt, neurotrophin, and solvent. Preferably, the concentration of reducing agent is about 0.5 to 8 mM, more preferably about 0.5–5 mM, even more preferably about 0.5–2 mM. The preferred reducing agents are DTT and cysteine.

Oxygen in the refold solution may optionally be depleted by addition of an inert gas, for example helium or argon, to displace the oxygen.

The optional osmolyte is preferably sucrose (in a concentration of about 0.25–1M) or glycerol (in a concentration of about 1–4M). More preferably, the sucrose concentration is at about 1M and the glycerol concentration is at about 4M.

The initial concentration of neurotrophin in the folding buffer is such that the ratio of correctly folded to misfolded conformer recovered will be maximized, as determined by HPLC, RIA, or bioassay. The preferred concentration of neurotrophin (resulting in the maximum yield of correctly folded conformer) is in the range of about 0.1 to 15 mg/mL, more preferably about 0.1 to 6 mg/mL, and most preferably about 0.2 to 5 mg/mL.

The degree of refolding that occurs upon this incubation is suitably determined by the RIA titer of the neurotrophin or by HPLC analysis with increasing RIA titer or correctly folded neurotrophin peak size directly correlating with increasing amounts of correctly folded, biologically active neurotrophin conformer present in the buffer. The incubation is carried out to maximize the yield of correctly folded neurotrophin conformer and the ratio of correctly folded neurotrophin conformer to misfolded neurotrophin conformer recovered, as determined by RIA or HPLC, and to minimize the yield of multimeric, associated neurotrophin as determined by mass balance. Alternatively, the species can be determined via the methods provided below and in the Examples. Guanidine is a preferred denaturing agent for refolding.

After the neurotrophin is refolded, the following procedures as taught herein, individually or in combination, are exemplary of suitable purification procedures for obtaining greater purity and homogeneity: fractionation on cation-exchange columns; hydrophobic interaction chromatography (HIC); and chromatography on silica.

Whether a refolding step is part of the process or not, a preferred step for separation of a neurotrophin from its variants is separation on hydrophobic interaction chromatography resin. During fermentation, purification or in vitro protein refolding, some protein can be chemically modified, misprocessed, or may not refold to its native three-dimensional structure but rather to other structures which differ with respect to their stability, solubility, immunogenicity, or bioactivity. These variants must be removed during recovery to avoid undesirable side-effects such as antigenicity or loss of potency. If the variant is insoluble it can be easily removed by solid/liquid separation techniques such as centrifugation and filtration. However, if the variant is soluble, higher resolution adsorption techniques such as chromatography will be required to remove them. When produced in prokaryotic cells or when refolded in vitro, neurotrophins form a soluble stable misfolded variant. Misfolded neurotrophin has an altered disulfide pairing pattern and three-dimensional structure relative to native neurotrophin and lacks native pharmacological activity. When produced in eucaryotic cell culture, e.g. mammalian cell culture, the variant forms are typically misprocessed forms. These also typically lack native pharmacological activity and should be removed. HIC has been found herein as suitable for separating these variants from native neurotrophin.

HIC involves sequential adsorption and desorption of protein from solid matrices mediated through non-covalent hydrophobic bonding. Generally, sample molecules in a high salt buffer are loaded on-the HIC column. The salt in the buffer interacts with water molecules to reduce the salvation of the molecules in solution, thereby exposing hydrophobic regions in the sample molecules which are consequently adsorbed by the HIC column. The more hydrophobic the molecule, the less salt needed to promote binding. Usually, a decreasing salt gradient is used to elute samples from the column. As the ionic strength decreases, the exposure of the hydrophilic regions of the molecules increases and molecules elute from the column in order of increasing hydrophobicity. Sample elution has also be achieved by the addition of mild organic modifiers or detergents to the elution buffer. HIC is reviewed in Protein Purification, 2d Ed., Springer-Verlag, New York, pgs 176–179 (1988).

The strength of the association between a protein and a matrix depends on several factors, including the size and hydrophobic character of the immobilized functional group, the polarity and surface tension of the surrounding solvent, and the hydrophobicity of the protein. The binding capacity of HIC matrices tends to be low due to the need for the immobilized hydrophobic ligand to be widely spaced. Further, the capacity of a medium for a given protein varies inversely with the level of hydrophobic impurities in the sample preparation. In order to resolve a desired protein from variants and other impurities while simultaneously maximizing capacity, it is necessary to identify a suitable HIC solid-phase medium as well as suitable mobile phases for load, wash, and elution.

As determined herein, the most suitable media for separating correctly folded and misfolded neurotrophins or misprocessed forms from intact, correctly processed forms, were those having immobilized phenyl functional groups. Phenyl-based HIC media from different vendors exhibited different efficiency for resolving these neurotrophin forms. Best results were achieved with Phenyl Toyopearl media by TosoHaas and Phenyl Sepharose Fast Flow Low Sub (low substitution). TSK Phenyl 5PW was also suitable. Other HIC-immobilized functional groups can function to separate these forms. Examples were octyl groups, such as those on Octyl Sepharose CL4B media from Pharmacia, and propyl groups, such as those on High Propyl media from Baker. Less preferred are the alkoxy, butyl, and isoamyl functional group resins.

HIC was useful for separation of neurotrophins from their variants in mammalian cell culture. For example, as was determined herein, rhNGF-expressing-CHO cell culture contained incorrectly proteolytically processed variants, such as those in which a partial precursor sequence is present, e.g., precursor NGF, hybrid precursor NGF, and clipped precursor NGF sequences. Also found in the mammalian cell culture medium were glycosylated NGF and glycosylated forms of the incorrectly proteolytically processed variants. Undesirable glycosylated forms, which in the case of NGF can be seen as a higher molecular weight species (+2000 kD), could generate an unwanted antigenic response in a patient and contribute to poor product quality or activity. HIC effectively separated hydrophobic variants, primarily N-terminal-proteolytically-misprocessed variants, including glycosylated forms, from rhNGF. As shown in the examples, the precursor-sequence-containing and clipped precursor sequence NGF and the glycosylated forms of both NGF and the precursor-sequence-containing NGF eluted in the leading edge of the NGF peak during phenyl-HIC. Thus, a rhNGF composition could be obtained that was substantially free of these species, and that was particularly suited for a subsequent step such as high performance cation-exchange chromatography. HIC is applicable to other neurotrophins, as well as NGF, regardless of source. For example, HIC is useful to separate NGF monomers from dimers, either homo- or hetero-dimers depending on the monomer forms present, as well as distinguish dimer forms which also differ in hydrophobicity, that are obtained after in vitro refolding or when produced and secreted from mammalian cells. A preferred source of neurotrophin mixtures for use with HIC is mammalian cell culture, more preferably CHO cell culture. The culture is preferably subjected to at least one prior purification step as discussed herein. HIC is particularly effective in separating misprocessed glycosylated variant(s) from the native recombinant neurotrophin. In the case of rhNGF, the glycosylated and preproNGF forms are less hydrophobic than native NGF, thereby eluting before native NGF. Misfolded forms of neurotrophins (when bacterially produced) are also more hydrophobic, eluting earlier than the native neurotrophin.

The most preferred HIC resin for separating neurotrophin forms were those having immobilized phenyl functional groups. Phenyi-based HIC media from different vendors exhibited different efficiency for resolving these NGF forms. Of the phenyl-HIC resins, Phenyl Toyopearl media by TosoHaas is most preferred and Phenyl Sepharose Fast Flow Low Sub (low substitution) and TSK Phenyl 5PW are preferred. Preferred HIC functional groups include the alkoxy, butyl, and isoamyl moieties.

Using HIC, a variety of mobile phase conditions can be used to wash and differentially elute neurotrophin forms. These mobile phases can contain several different chemical species that influence the association between a neurotrophin and the stationary phase in different ways. Correctly folded and misfolded neurotrophin, e.g. NT-4/5, can be resolved on a HIC column by decreasing salt gradients or step-wise decrease, for example of mobile-phase salt, e.g., ammonium sulfate, NaCl concentration, acetate concentration. Salts can influence the binding of a neurotrophin to the resin by modulating the surface tension of the mobile phase. Other agents that affected surface tension were sodium citrate and tetramethyl ammonium chloride, as discussed in the Examples. Variants can also be resolved during column chromatography by eluting bound protein with increasing gradients or step-wise increase in concentration of relatively polar organic solvents. Examples of suitable solvents include ethanol, acetonitrile, and propanol. The strength of the association between neurotrophin forms and HIC resin also depended on the mobile-phase pH, with neutral conditions preferred. The relative hydrophobicity of correctly folded and misfolded neurotrophin also depended on solution pH. Separation of variants from native neurotrophin could also be obtained by simultaneously varying several properties of the mobile phase during gradient or stepwise elution. For example, a mobile phase that simultaneously varied in salt concentration and apolar solvent concentration during elution provided resolution better than when only salt was varied.

For HIC, salts discussed herein, including ammonium sulfate, citrate, acetate, and potassium chloride can be used. Depending on the salt used, the salt concentration is typically 0.5 M to 3 M, more preferably 0.5 to 2.5M, to achieve binding of neurotrophin to the resin. For example, a binding buffer of 0.8 to 1.5 M salt is preferred for NGF, with higher salt concentrations leading to precipitation of NGF onto the resin resulting in lower recovery. For NT-3 a binding buffer at pH 7 with a salt concentration of 1.0 to 2.5 is preferred, with 1.25 to 1.75 M NaCl being more preferred, and 1.5 M most preferred. For NT-4/5 a binding buffer at pH 7 with 1 to 3 M salt is preferred, with 2 to 2.75 M being more preferred, and 2.5 M NaCl being most preferred. In the case of NT-4/5, when 2.5 M NaCl was preferred for loading, 2M NaCl was preferred for elution with organic solvent present (e.g. 10% alcohol, pH 7). Preferably, a lowering of the salt concentration is used to elute and separate a neurotrophin and its variants. In order to achieve elution, the salt concentration in the elution buffer is typically lower than that in the loading -buffer, but it can be the same concentration when compensated for with organic solvent.

In addition, the use of organic solvent has another advantage, as has been found herein, that the addition of an organic solvent improves the elution pattern by resulting in narrower peak profiles. In addition to ethanol, other organic solvents discussed herein can be used, including propanol, isopropanol, and lower alkylene glycols, such as propylene glycol, ethylene glycol and hexylene glycol. The organic solvent at 5 to 25% (v/v), more preferably 5 to 20% (v/v), will typically elute a correctly folded neurotrophin. The elution with organic solvent can be either gradient or step-wise. The pH range is preferably near neutral to slightly acidic, from pH 5 to 8, more preferably pH 6 to 8, pH 6.5 to 7.5, and most preferably pH 7. Any of the buffers discussed herein, including MOPSO, MOPS, HEPES, phosphate, citrate, ammonium, acetate, can be used as long as they buffer at the desired pH.

In view of the discovery by the present inventors of certain undesirable neurotrophin variants arising from recombinant production of a neurotrophin, as reported herein, the use of high performance cation-exchange chromatography, preferably in preparative mode, allows separation of the charge-modified variants, such as carbamylated, oxidized, isoasp, deamidated, and certain clipped forms (e.g. C-terminal truncated forms of NGF) from native neurotrophin. For example, N-terminal clipped forms (e.g., 2 to 4 N-terminal amino acid deletions) that result in charge alteration, which may occur during bacterial fermentation as in the case of NT-4/5 and NT-3, can now be removed. In the case of neurotrophins produced in mammalian cell culture, C-terminal truncation may occur in the highly charged terminal region. For example, 118 form of NGF may be niisprocessed or cleaved at its C-terminus to 117, 114 and 115 forms. These can be separated from native 118 NGF by high performance cation exchange chromatography. Particularly preferred embodiments use SP-Sepharose High Performance, Fractogel EMD SO3, or polyaspartic acid resin, of which PolyCAT A is particularly preferred. Most preferably, at large scale, SP-Sepharose High Performance or Fractogel EMD SO3 resins are used.

Compositions obtained by the processes described herein will be substantially pure neurotrophin, more usually and preferably essentially pure, and will be substantially free of neurotrophin variants, more preferably essentially free of neurotrophin variants. For example, a typical SP-Sepharose pool after purification of NGF from CHO cell culture, contains about 92% 118, 4.6% 120, 1% deamidated NGF, 1% oxidized NGF, and 1%isoasp NGF. Routinely the amount of each species ranges from about 85 to 93% for 118, 0 to 5% for 120 (depending in large part on the extent of endogenous and/or exogenous proteolysis that is used), 0 to 5% for 117, 0 to 3% for deamidated forms, 0–2% for isoasp forms, and 0 to 2% for oxidized forms. The purity of NGF (all species) is routinely greater than 99.5%.

After the neurotrophin is eluted from the column, it is suitably formulated into a composition with a carrier, preferably a pharmaceutical composition with a physiologically acceptable carrier. Neurotrophin compositions are preferably sterile. The neurotrophin compositions of the invention also find use in in vitro, for example, to promote growth and survival of neurons in culture.

The chemical and physical stability of recombinant human nerve growth factor (NGF) in aqueous solution was investigated between 5 and 37° C., in the pH range 4.2 to 5.8. NGF chemical stability increased with increasing pH. In succinate buffer at pH 5.8, NGF physical stability decreased due to protein aggregation. Based on both the 5° C. stability data and accelerated degradation studies at 37° C., the optimal formulation was found to be acetate buffer at pH 5.5. (see WO 97/17087 which is incorporated herein by reference) Reversed-phase HPLC was the primary stability indicating method, showing conversion of Asn-93 to iso-Asp to be the primary degradation pathway at 5° C. Quantitation of NGF degradation by cation exchange chromatography was complicated by the rearrangement of the NGF monomer variants into various mixed dimers over time (dimer exchange). Treatment of samples and controls with dilute acid rapidly equilibrated the monomer distribution in the dimers, allowing NGF degradation to be quantitated in the absence of dimer exchange. Benzyl alcohol and phenol were evaluated for their compatibility and stability with rhNGF in two liquid formulations for multi-use purposes. These two formulations consist of 0.1 mg/ml, protein in 20 mM sodium acetate at pH 15.5 and 136 mM sodium chloride with and without 0.01% pluronic acid (F68) as surfactant. The final concentrations of benzyl alcohol and phenol in each of these two formulations were 0.9 and 0.25%, respectively. Based on the 12 month stability data, rhNGF is more stable with benzyl alcohol than phenol in these formulations. Benzyl alcohol preserved rhNGF formulation with the presence of surfactant is as stable as the formulation with no surfactant added, indicating that the addition of F68 to rhNGF multi-dose formulation is not required for stability purpose. Therefore, a formulation consisting of 0.1 mg/mL protein in 20 mM acetate, 136 mM NaCl, 0.9% benzyl alcohol, pH 5.5 is recommended for rhNGF used for multiple dosing in Phase III clinical trails. This rhNGF multi-dose formulation passed the USP and EP preservative efficacy test after 6 months at 5° C., and is as stable as the current liquid formulation at 2 mg/mL. However, the formulation should avoid exposure to intensive light due to the presence of benzyl alcohol as preservative which is light sensitive.

In general, the compositions may contain other components in amounts preferably not detracting from the preparation of stable, liquid or lyophilizable forms and in amounts suitable for effective, safe pharmaceutical administration.

Neurotrophin is formulated with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides. This formulation step is achieved by desalting or diafiltering using standard technology.

Generally, the formulations are prepared by contacting the neurotrophin uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, trehalose, glucose, mannose, or dextrins; chelating agents such as EDTA, sugar alcohols such as mannitol or sorbitol; counter-ions such as sodium; and/or nonionic surfactants such as polysorbates, poloxamers, or PEG. The final preparation may be a liquid or lyophilized solid.

Neurotrophin to be used for therapeutic administration must be sterile. Sterility is readily accomplished by filtration through sterile filtration membranes (e.g., 0.2 micron membranes). Therapeutic neurotrophin compositions generally are placed into a container having a sterile access port, for example, an intravenous solution bag or vial having a stopper pierceable by a hypodermic injection needle. The above formulations are also suitable for in vitro uses.

Neurotrophin ordinarily will be stored in unit or multi-dose containers, for example, sealed ampules or vials, as an aqueous solution, or as a lyophilized formulation for reconstitution. As an example of a lyophilized formulation, 10-mL vials are filled with 5 mL of sterile-filtered 1% (w/v) aqueous neurotrophin solution, and the resulting mixture is lyophilized. The infusion solution is prepared by reconstituting the lyophilized neurotrophin using bacteriostatic Water-for-Injection.

A therapeutically effective dose of an neurotrophin formulation is administered to a patient. By "therapeutically effective dose" herein is meant a dose that produces the effects for which it is administered. The exact dose will depend on the disorder to be treated, and will be ascertainable by one skilled in the art using known techniques. In general, the neurotrophin formulations of the present invention are administered at about 0.01 mu.g/kg to about 100 mg/kg per day. Preferably, from 0.1 to 0.3 ug/kg. In addition, as is known in the art, adjustments for age as well as the body weight, general health, sex, diet, time of administration, drug interaction and the severity of the disease may be necessary, and will be ascertainable with routine experimentation by those skilled in the art. Typically, the clinician will administer neurotrophin formulations of the invention until a dosage is reached that repairs, maintains, and, optimally, reestablishes neuron function. The progress of this therapy is easily monitored by conventional assays.

Neurotrophin optionally is combined with or administered in concert with other neurotrophic factors including NGF, NT-4/5, NT-3, and/or BDNF and is used with other conventional therapies for nerve disorders.

In the case of NGF, preferably a composition comprises a pharmaceutically effective amount of nerve growth factor and a pharmaceutically acceptable acetate-containing buffer. The composition can have a pH from pH 5 to 6. The buffer is preferably sodium acetate. The acetate concentration is preferably 0.1 to 200 mM. The composition preferably has an NGF concentration of 0.07 to 20 mg/ml. And, the composition optionally further contains a pharmaceutically acceptable preservative, such as benzyl alcohol, phenol, m-cresol, methylparaben, or propylparaben. Preferably the preservative is benzyl alcohol. The benzyl alcohol concentration is preferably from 0.1 to 2.0%. The composition can optionally contain a pharmaceutically acceptable surfactant. And, the composition can optionally, but preferably, contain a physiologically acceptable concentration of sodium chloride. A more preferred composition contains nerve growth factor at a concentration of at least about 0.1 mg/ml and an acetate ion concentration of 10 mM to 50 mM. Even more preferably, the composition contains nerve growth factor at a concentration of 0.1 to about 2.0 mg/ml and acetate ion at a concentration of 10 mM to 50 mM. A most preferred composition contains NGF at a concentration of 0.1 mg/ml, sodium acetate concentration of 20 nM, pH 5.5, sodium chloride concentration of 136 mM, and benzyl alcohol at 0.9% (v/v).

Another embodiment contains an NGF concentration of 2.0 mg/ml a sodium acetate concentration of 10 mM, pH 5.5, and a sodium chloride concentration of 142 mM. It is preferable to formulate NGF with 0.1 mg/ml, 20 mM sodium acetate, 136 mM sodium chloride, 0.9% (v/v) benzyl alcohol, at a pH of 5.5. As discussed herein, the 118/118 homodimer is a preferred form of NGF. NGF is purified at about pH 6 to 8 to maintain the normal dimer form. However, the percentage of (proteolytically) clipped forms represents monomeric forms, which become apparent and can be determined by reversed-phase HPLC. The acid conditions of the analytical HPLC dissociates the dimers. The existence of different dimeric forms of NGF—120/120, 120/118, 118/118, etc.—has been published (Schmelzer et al. J. Neurochem. 59:1675–1683 (1992), which is specifically incorporated herein in its entirety, mainly for its analytical and bioassays that were used in the current studies as well as for its general teachings). That publication reported that the in vitro activities were the same for each dimeric form. However, in contrast, the present studies herein demonstrate for the first time that the 120/120 dimer is less active, about 80–90% as active, as the 118/118 species, using a radioreceptor based assay. In one form of the assay, rat PC-12 cells membranes are isolated and used for competitive binding between NGF standard and the various test species. The RRA has both P75 and trkA receptors. It was also found herein that the 117/117 species is as active as the 118/118 species. Furthermore, use herein of a PC-12 based assay confirmed the receptor-based assay finding, showing that the 120/120 form is about 60% as active as the 118/118 form. Also incorporated in its entirety specifically by reference is Burton et al, J. Neurochem. 59:1937–1945 (1992) mainly for its analytical and bioassay that were used in the current studies as well as for its general teachings.

The 118/118 form is believed to be more bioavailable in human patients than the 120/120 form. The increase in bioavailability is at least 4 to 5 fold. This difference is significant, surprising, and unexpected in view of the art.

The following examples are offered by way of illustration and not by way of limitation. The disclosures of all citations in the specification are expressly incorporated herein by reference.

EXAMPLES

Example 1

Purification of 118/118 NGF Homodimer

This example illustrates purification of NGF and the rationale for each step. As in each of the Examples, one skilled in the art can readily determine and adjust column dimensions and flow rates to compensate for initial culture volumes and protein concentrations as is well-known in the art.

Harvested Cell Culture Fluid

Recombinant CHO cell was transfected with an expression vector containing the 120 amino acid human NGF encoding DNA sequence. To promote secretion and processing the NGF prepro sequence was also present. After culturing of the recombinant CHO cells, the cell culture medium was harvested. The Harvested Cell Culture Fluid (HCCF) contained NGF. species 120, 118, and 117. About 40–70% of the NGF was typically a 118/118 homodimer with the remainder as heterodimers 120/118, 120/120, and a small amount as 118/117. As taught herein, these species can be separated by the SP-Sepharose HP column.

Harvested Cell Culture Fluid was concentrated approximately 20-fold using Millipore 10 Kd cutoff membranes (either cellulose, composite or polysulfone were used interchangeably). To the concentrate was added 0.1 volumes of 1.0 M Tris, pH 8.2. The diluted material was microfiltered using a 0.22 um filter and transferred to a holding tank at 37 degrees C. for 2 to 18 hours. Conversion of 120/120 form to the 118/118 form is catalyzed by an endogenous protease during holding.

Silica Gel Chromatography

The microfiltrate was adjusted to 1M NaCl and applied to a Silica Gel Column equilibrated in 1M NaCl, 25mM MOPSO, pH 7. The column was washed with 1M NaCl, 25 mM MOPSO, pH7. Suitable pH range is about pH 6 to 8, with a preferred pH of 7. The column was then washed with 25 mM MOPSO, pH 7. A low conductivity wash removes host cell proteins. Bound NGF was eluted with 50 mM MOPSO, 0.5 MT MAC, 20% reagent anhydrous grade alcohol (94–96% Specially Denatured alcohol formula 3A (5 volumes of methanol and 100 volumes of 200 proof ethanol) and 4–6% isopropanol). Other alcohols can be used such as 20% propanol, 20% isopropanol and 20% methanol. As used herein, "alcohols" and "alcoholic solvents" are meant in the sense of the commonly used terminology for alcohol, preferably alcohols with 1 to 10 carbon atoms, more preferably methanol, ethanol, iso-propanol, n-propanol, or t-butanol, and most preferably ethanol or iso-propanol. Such alcohols are solvents that, when added to aqueous solution, increase the hydrophobicity of the solution by decreasing solution polarity. Ethanol is most preferred. The lower limit of alcohol is whatever percentage that elutes and the upper limit is set by the need to avoid protein denaturation. The solvent is preferably 5% to 25%, more preferably 5 to 20%, even more preferably 5 to 15%. TMAC is tetramethyl ammonium chloride, which is present to elute NGF. TMAC can range from 0.1 to 1 M. With the range 0.3 to 0.7 M being more preferred. The amount of TMAC used to elute NGF is a function of pH and alcohol concentration. The lower the pH the less amounts of alcohol and TMAC is required. The pH can be between about pH 4 to 8. In this example the preferred pH was 7, which allows very minimal adjustment of the pooled fractions prior to loading onto the next column. The upper pH limit is determined by the pH necessary to load the next column, and the lower limit by that useful to elute NGF efficiently.

S-Sepharose Fast Flow Chromatography

The eluant containing NGF was pooled, diluted to a conductivity of less than 15.5 ms/cm with purified water, and pH adjusted to 7.0. The material was held no longer than 8 hours since several proteases were still present; however, no activity of the endogenous protease that converts 120 amino acid NGF to 118 form was observed. The material was applied to an S-Sepharose Fast Flow chromatography column (a cation-exchange resin S-SEPHAROSE TM agarose Fast Flow TM (Pharmacia)) equilibrated in 25 mM MOPSO, pH 7. The column is washed with 25 mM MOPSO, pH 7. A suitable pH range is from about pH 6 to 8, with pH 7 preferred. The column was then washed with 0.16 M NaCl, pH 7. The bound NGF was eluted with 0.5 M NaCl, pH 7. The elution salt molarity can range from 0.3 to 1.0 M, more preferably 0.4 to 0.6 M. The lower limit is set by the usefulness to elute all the NGF, and the upper limit is set by the need to avoid removing contaminants and causing hydrophobic interactions on the column which would interfere with elution of NGF. Other salts can be used, KCl being a preferred alternative. Elution with 0.5 M NaCl, pH 7, is preferred in order to obtain a pool with a small volume. At higher salt concentrations, e.g., over 1 M, tightly bound contaminants may elute.

Phenyl Toyopearl 650M Chromatography

SSFF column fractions containing NGF were pooled, adjusted to 1 M NaCl, and applied to a Phenyl Toyopearl 650M column. The column was washed with 25 mM MOPSO, pH 7. A suitable pH is in the range of about pH 5 to 8. The bound NGF was eluted with a 10CV (column volume) linear gradient beginning with gradient buffer A (25 mM MOPSO, pH 7, 1.0 M NaCl) and ending with gradient buffer B (20%. alcohol in 80% 25 mM MOPSO, pH 7). Fractions containing NGF were analyzed by SDS-PAGE polyacrylamide gel electrophoresis to determine which fractions harbored the precursor NGF species. Fractions containing NGF and were selected and pooled to remove primarily incorrectly processed variants, such as those in which a partial precursor sequence is present, e.g., precursor NGF, hybrid precursor NGF, and clipped precursor NGF sequences, to obtain an NGF composition substantially free of any NGF precursor sequences. The phenyl column also removed the small amount of glycosylated NGF and glycosylated NGF precursor sequences. The precursor and clipped precursor NGF sequences along with the glycosylated forms of both NGF and precursor NGF eluted in the leading edge of the NGF peak. Thus, this column readily separated NGF from various NGF species to obtain an NGF composition substantially free of these species. In this step variant NGF hydrophobic variants, primarily misprocessed variants, including proteolytic and glycosylated variants, were separated using HIC.

The most suitable media for separating NGF forms were those having immobilized phenyl functional groups. Phenyl-based HIC media from different vendors exhibited different efficiency for resolving these NGF forms. Best results were achieved with Phenyl Toyopearl media by TosoHaas. HIC resins Phenyl Sepharose Fast Flow Low Sub (low substitution) and TSK Phenyl 5PW worked well. Other HIC functional groups were less suitable, and less effective, under these conditions, including the alkoxy, butyl, and isoamyl moieties.

The PhenylToyopearl pool contained 75% 118, 10% 120, 7% 117, 1.8% deamidated NGF, 1.4% oxidized NGF, and 2.0% isoasp NGF, with the remaining 2.8% being other unidentified NGF species.

Optionally, the pooled fractions were acid treated to achieve viral inactivation at a pH less than 3.95 for a minimum of 15 minutes.

SP-Sepharose HP Chromatooraphy

The HIC pool was diluted with 0.5 to 1 volumes of water and the diluted pool was adjusted to pH 6. The pool was loaded onto an SP-Sepharose HP column equilibrated with 0.2 M sodium chloride, 20 mM succinate, pH 6, containing 5% reagent alcohol (as in the Silica gel column step). The column was washed with 0.2 M NaCl, 20 mM succinate, pH 6 containing 5% reagent alcohol (Formula SDA-3A alcohol; the alcohol is optionally present). Alcohol helps reduce non-specific (mostly hydrophobic) interactions of NGF with the resin backbone. A suitable alcohol range is from about 0 to 10%. The loading pH is from about pH 5 to 8, which is chosen to achieve and maintain maximal stability of NGF and separation of NGF variants. The column was washed with two column volumes of equilibration buffer. Bound NGF was eluted and separated from variants by a linear 22-column-volumes gradient by mixing of 11 column volumes of gradient buffer A (0.25 M NaCl, 0.02 M succinate, pH6, containing 5% alcohol) and 11 column volumes of gradient buffer B (0.5 M NaCl, pH 6). The alcohol is optional. The 118/118 NGF typically eluted at 0.35 M to 0.40 M NaCl concentration.

The column fractions were analyzed for NGF and variant NGF content. Fractions are preferably analyzed by C4 RP-HPLC as described by Schmelzer et al. (1992), supra., and Burton et al. (1992), supra. Fractions were selected and pooled to obtain a composition of NGF that was substantially free of modified NGF variants, e.g., charged species such as oxidized, deamidated and isoasp NGF species. The previous HIC column cannot effectively remove other variant forms of NGF such as oxidized and isoasp NGF. The HIC column does effectively remove misfolded proteins and glycosylated, which bind tighter to the HIC resin than correctly folded NGF, since they tend to be more hydrophobic. Accordingly, the cation exchange resin, e.g., SP-Sepharose HP, was used to remove altered charge variants not removed by the HIC resin.

The SP-Sepharose pool typically contained about 92% 118, 4.6% 120, 1% deamidated NGF, 1% oxidized NGF, and 1% isoasp NGF. Routinely the amount of each species ranges from about 85 to 93% for 118, 0 to 5% for 120, 0 to 5% for 117, 0 to 3% for deamidated forms, 0–2% for isoasp forms, and 0 to 2% for oxidized forms. The purity of NGF (all species) is routinely greater than 99.5%.

Formulation

The SP-Sepharose HP pool was prepared for formulation by ultrafiltration/diafiltration into a formulation buffer. An acidic buffer is preferably used, preferably acetate at pH 5 as discussed above. The 118/118 NGF composition is substantially free of NGF variants and is substantially pure NGF. The formulated material is suitable for treating neuronal disorders, particularly peripheral neuropathy associated with diabetes and peripheral sensory neuropathy associated with AIDS.

Example II

Purification of the 120/120 NGF Homodimer at Large Scale

Harvested Cell Culture Fluid

HCCF was obtained from a 12,000 liter CHO cell culture generally as described in Example I. The NGF species distribution in the HCCF was about 40–65% 120/120 homodimer with 120/118 heterodimer with the remaining as 118/118 homodimer. The medium was typically quickly processed to minimize proteolytic conversion of 120 to 118.

Macroprep High S Cation-Exchange Chromatography

The HCCF was loaded onto a Macroprep High S Cation-Exchange Chromatography column, washed with 1.5 M sodium acetate, 50 mM HEPES pH 7. Bound NGF was eluted with 1.5 M NaCl, 0.25 M TMAC, 0.2% thiodiglycol, pH 7. The Macroprep column can be run at pH 5 to 8 with adjustment of the acetate concentration. Chloride is a preferred substitute for acetate ion. The NGF eluted due to the TMAC gradient. TMAC is a salt having both ionic and hydrophobic character, which is a useful property since the backbone support of some resins contains hydrophobic content that promotes non-specific interactions between NGF and the resin. Typically, for an elution buffer of pH from about pH 6 to 8, a 0–3 M TMAC concentration is useful. Fractions containing NGF were pooled.

Silica Gel Chromatography

The pool was directly applied to a Silica Gel Chromatography Column. Silica provides a mixed mode chromatography resin, having ionic, polarity, and hydrophobic interactions that play a part in protein binding characteristics. The column was equilibrated in 1M NaCl, 25 mM MOPSO,-pH 7. The column was washed with 1M NaCl, 25 mM MOPSO, pH7 (preferably about pH 5.0 to 8.5, more preferably pH 6 to 8, and most preferably pH 7). Bound NGF was eluted with 25 mM succinate, pH 3.9, 50 mM TEAC (tetraethylammonium chloride). TEAC is a more powerful eluant than TMAC. The pH preferably ranges from about pH 3.5 to 8. However, a pH above 7.5 for extended periods of time should be avoided in order to prevent or reduce formation of the deamidated NGF species. Generally, the lower the pH of the buffer, the lower the concentration of the mixed-property salt, e.g., TMAC or TEAC, required to elute NGF from the Silica column. Buffers having a good buffering capacity near pH 4 to 5 are suitable for use. The presence of salt in the elution buffer is optional, such that the column can be washed with a MOPSO buffer without salt prior to application of the elution buffer.

Phenyl Sepharose Fast Flow Chromatography

The fractions containing NGF were identified and pooled. The pool was adjusted to 0.7 M acetate, pH 7, 25 mM MOPSO. The adjusted pool was loaded onto a Phenyl Sepharose Fast Flow Chromatography column equilibrated with gradient buffer A (0.7 M acetate, 25 mM MOPSO, pH 7). The column was washed with a gradient from 90% gradient buffer A (0.7 M acetate, 25 mM MOPSO, pH 7) to 10% gradient buffer B (25 mM MOPSO, pH 7, 20% propylene glycol). Other glycols can be substituted, such as hexylene glycol. Typically the wash was about 2 to 3 CV or until a stable baseline OD is achieved. The wash removed some host cell proteins. Bound NGF was eluted with a linear 10 CV gradient from a mix of 90% gradient buffer A and 10% gradient buffer B to a mix of 10% gradient buffer A and 90% gradient buffer B. NaCl or sodium sulfate can substitute for acetate in the HIC buffers. The pH is preferably from about pH 5 to 8, more preferably about 5.5 to 7.5, with pH 6 to 8 acceptable, and most preferably about pH 7. The column separated any remaining precursor sequences, partial precursor sequences, or glycosylated forms, present as a homodimer or as a heterodimer of a mature NGF monomer and a NGF monomer that still has part of the precursor sequence present. The precursor and glycosylated forms of NGF are present in the leading edge of the elution peak, such that NGF-containing fractions were pooled to substantially exclude these species.

The HIC pool contained about 72% 120 monomer, 17% 118 monomer, 2.8% 117 monomer, .3.6% R120 monomer, 0.8% isoasp forms, 1.3% oxidized forms, and 1% deamidated forms, as separated and detected on an analytical HPLC system.

SP-Sepharose HP Chromatography

Fractions containing NGF from the HIC-step were pooled. At large scale this was accomplished by directing the column effluent at the appropriate time to a pool tank (holding tank). The pH of the pool was adjusted to pH 6, and applied to a SP-Sepharose HP Chromatography column. The column was washed with 20 mM succinate, 0.2 M NaCl, pH 6 (gradient buffer A). The bound NGF was eluted with a 22 CV gradient beginning with a mixture of 70% gradient buffer A and 30% gradient buffer B to a final mixture of 80% gradient buffer B (0.7 M NaCl/pH 6) and 20% gradient buffer A. The pH is preferably from pH 5 to 8, more preferably pH 5.7 to 6.5, and most preferably pH 6. A representative chromatogram is shown in FIG. 1.

The SP-Sepharose HP pool routinely contained about 95% 120 form, 3% R120 form, 0.65% isoasp form, 0.6% oxidized form, 0.6% deamidated form. Other unidentified forms of NGF were at about 0.6%, and comprised of di-oxidized NGF (Met37 and Met 92) with a deamidated Asn45 present. An HPIEX analysis comparing a representative HIC pool (loaded onto the SP-Sepharose resin) and the pool obtained after SP-Sepharose chromatography is shown in FIG. 2. Each of the three major clipped forms of NGF, 120, 118, and 117, may have variants, but the variants, such as oxidized and isoasp forms, of the predominant clipped form during a purification (120 in this example) may mask analysis of the variants from the less predominant forms (118 and 117 in this example). An HPLC analysis of fractions from a representative run is shown in FIG. 3.

The SP-Sepharose HP effectively removed variants present in the HIC pool. The R120 form has an additional arginine residue at the N-terminus of NGF; usually the N-terminal amino acid sequence of rhNGF is SSSHP, but R120 has an N-terminal sequence of RSSSHP. Thus the R120 form is more basic than mature NGF and was separated by SP-SHP. It also has lower bioactivity, probably related to the fact that the NGF N-terminal is necessary for receptor (trkA) binding. The oxidized NGF form is a mono-oxidized form having the methionine at position 37 oxidized, yielding a more acidic form that elutes on the leading edge of the NGF peak. The isoasp form contains a modification of the aspartic acid at amino acid 93. The isoasp form is slightly more basic and thus binds slightly tighter to the SP-Sepharose HP resin. NGF species containing isoAsp93 eluted in the trailing edge of the elution peak. Deamidation occurs at asparagine residues, typically at asparagine at position 45. NGF containing deamidated Asn, which yields an Asp at position 45, is slightly more acidic, appearing at the leading edge of the elution peak.

Fractogel EMD SO3 is a less preferred alternative resin to SP-Sepharose HP resin for separating charged variants of the NGF species. When using this less preferred resin, higher concentrations of NaCl are needed to elute NGF.

Formulation

The bulk material was formulated by UF/DF into formulation buffer as in the prior Example. In the final bulk product, the 120 form ranged routinely from about 92 to 97%, the R120 from about 1 to 4%, the isoasp form from about 0.2 to 1.5%, the oxidized form from about 0.2 to 2%, and the deamidated form from about 0.2 to 2%. The 117 and 118 forms were routinely less than about 2%. The final bulk product was routinely at least 99.5% pure NGF (including all species).

Example III

Isolation of 118/118

In one preferred embodiment to obtain a substantially pure 118/118 NGF composition that is substantially free of NGF variants, the method of Example It was followed with the following modifications. An immobilized trypsin column is used between the Macroprep High S column and the Silica column. The Macroprep pool is directly loaded onto the immobilized trypsin column, after adjusting the pH to between about pH 5 to 8.5, most typically 6.5 to 7.5, if necessary. The pool was passed through the column during which time most of the NGF was converted to the 118 form. The protease digestion converts the 120 form to the 118 form by cleavage of the C-terminal VRRA to VR. To achieve the limited and selective cleavage, a trypsin or trypsin-like protease is used, preferably trypsin, more preferably the readily available porcine trypsin, or alternatively bovine trypsin or a recombinant trypsin. Any proteolytic method that provides substantially limited and selective cleavage can be used, but preferred is an immobilized-trypsin column in order to minimize contamination of the NGF preparation. The column is run at a pH conducive to protease activity, preferably pH 5.5 to 8.5, more preferably 6.0 to 8.0, and most preferably 6.5 to 7.5.

In this example, glycosylated NGF was removed by HIC as discussed herein. Following an SP-Sepharose HP step as discussed herein in Example II but preferably using a 22 column volume 0.3 M to 0.55M salt gradient, a preferred composition of NGF for clinical use was obtained. A composition of greater than 70% 118 monomer, less than 10% 120 monomer, and less than 15% 117 monomer, as determined by RP-HPLC assays, can be obtained. Typically compositions that are greater than or equal to 90% 118/118 rhNGF, more usually greater than or equal to 93% 118/118 rhNGF with less than or equal to about 7% deamidated, isoAsp and oxidized variants are obtained. One means to achieve higher purity is to avoid selecting fractions with significant amounts of variants, such as may be found in the leading or trailing edges of the main neurotrophin peak, e.g. 118/118 rhNGF peak.

Example IV

Partial Purification and Refolding of rhNT-4/5 from Bacterial Inclusion Bodies

In this example, starting with a 10 or 60 liter fermentation, rhNT-4/5 was purified. The host used to produce recombinant human NT-4/5 in the fermentation described in this example was an *E. coli* strain designated 27C7/pmNT5DT; although NT-4/5 produced from other strains and organisms is suitable for the purification process described herein. The expression plasmid used in this example contained the mature NT-4/5 coding sequence under transcriptional and translational control sequences required for expression of the NT-4/5 gene in *E. coli*. In the NT-4/5-expressing plasmid, the transcriptional sequences used for expression of the gene in *E. coli* were provided by the alkaline phosphatase promoter sequence. The lambda to transcriptional terminator was situated adjacent to the NT-4/5 termination codon. Secretion of the protein from the cytoplasm was directed by the STII signal sequence. The majority of rhNT-4/5 was found in the cell periplasmic space as refractile bodies. The plasmid conferred tetracycline resistance upon the transformed host. The fermentation process was performed at 35°–39° C. and pH 7.0–7.8. The fermentation was allowed to proceed for 25–40 hours, at which time the culture was chilled prior to harvest. The culture was inactivated by heat treatment using a continuous-flow apparatus at 60° C. or using in-tank heat inactivation at that temperature for 5–15 minutes. The heat-inactivated culture was centrifuged using a AX Alpha-laval centrifuge or equivalent. The *E. coli* cells were recovered in the pellet.

The *E. coli* cells, expressing recombinant human NT-4/5 in inclusion bodies, were lysed by standard means to prepare a paste containing NT-4/5 in inclusion bodies. No protease inhibitors were included in the buffer.

To isolate the inclusion bodies from cell debris, the *E. coli* NT-5 paste was resuspended in 0.02 M Tris, pH 8, 5 mM EDTA (10 ml of buffer/gram paste) using a rotary, mechanical dispersion device, for example a Turrax. The cell suspension was passed through a microfluidizer three times at 6000 psi. The resulting homogenate was centrifuged in a Sorvall RC-3B centrifuge at 5000 rpm for about 45 min. Supernatant was discarded and the pellet was resuspended in 20 mM Tris, pH 8, 5 mM EDTA (Extraction buffer) using a turrax for 2 to 3 minutes at medium speed. The homogenate was centrifuged as described above. The pellet was resuspended in extraction buffer and centrifuged as described above. The resulting pellet(s) (referred to as NT-4/5 inclusion bodies or refractile bodies) was stored at −70° C.

NT-4/5 was isolated from the inclusion bodies as follows. The inclusion body pellets were suspended in 20 mM Tris, pH 8, 6M Urea, 25 mM DTT (10 ml buffer/gram inclusion body) using a turrax at medium speed for about 10 min. The suspension was stirred for 40 min at 2–8° C. and centrifuged in a Sorvall RC3B at 5000 rpm for about 45 min. PEI (poly-ethylene-imine) was added to 0.1% in the supernatant, which was stirred at 2–8° C. for 30 minutes. The PEI precipitates nucleic acid and other acidic-charged molecules. The mixture was centrifuged in a Sorvall RC3B at 5000 rpm for about 45 minutes. The PEI supernatant was loaded onto a DEFF Sepharose Fast Flow column (10 cm×14 cm; DEFF is a diethyl aminoethyl resin) equilibrated in 0.02 M Tris, .6M Urea, 10 mM DTT, pH 8. An equivalent of 1 kg of solubilized refractile bodies was loaded onto the DEFF column. Since reduced and denatured NT-4/5 does not bind to the DEFF resin, the flow through pool containing NT-4/5 and 6M urea, was collected (FIG. 6) and the pH of the pool was lowered to 5.0 with acetic acid. The pH-adjusted DEFF flow through pool was loaded onto a S-Sepharose Fast Flow column (S refers to the SO3 functional group on the resin) equilibrated in 20 mM acetate, pH 5, containing 6M urea, under which conditions NT-4/5 binds to the resin. After loading, the S-Sepharose Fast Flow column was washed with several column volumes of equilibration buffer. The bound NT-4/5 was eluted with 0.5 M NaCl, 20 mM sodium acetate, 6M urea, pH 5 (FIG. 7). The 0.5 M NaCl SSFF pool was dialyzed overnight against 20 mM Tris, 0.14 M NaCl, pH 8, conditions that allow NT-4/5 to refold albeit incorrectly. The misfolded rhNT-4/5 molecules aggregated to form a precipitate.

The aggregated, misfolded rhNT-4/5 was processed to obtain correctly folded NT-4/5. The aggregated, misfolded rhNT-4/5 was collected by centrifugation as a pellet. The pellet was resuspended in 0.2 M Tris, pH 8, 4 M Urea, 5 mM DTT and stirred at 2–8° C. for about 1 to 2 hrs or until the pelt dissolved. The final protein concentration was adjusted to about 10 mg/ml protein based on the extinction coefficient 1.8 at 280 nm. Oxidized glutathione was added to the solubilized pellet solution to a final concentration of 20 mM, followed by gentle stirring for 15 to 30 min at 2–8° C. The oxidized glutathione reacts with the NT-4/5 sulfhydryl groups to yield NT-4/5-S-glutathione mixed disulfide. The NT-4/5-SG mixed disulfide were diluted to a final concentration of 0.1 to 0.5 mg/ml protein in 100 mM Tris, 20 mM glycine, 15% PEG-300, 1M Guanidine HCl, pH 8.3. To initiate proper refolding of NT-4/5, cysteine was added to the refold mixture at a concentration of 2 to 4 mM, followed by aeration (by bubbling through) of the solution with nitrogen or helium for 5 to 60 minutes before sealing the container to exclude oxygen. The refolding of NT-4/5 was allowed to proceed for 18 to 24 hrs at 2 to 8° C.

Alternatively, the rhNT-4/5 was refolded using sulfitolysis as follows. The inclusion body pellets (110 g) were suspended in 1.1 liter of 20 mM Tris, 7M Urea, 10 mM glycine, 100 mM sodium sulfite, 10 mM sodium tetrathionate, and solubilized using a turrax for 10 minutes at medium speed. The mixture (1260 mL) was then stirred at 2 to 8° C. for 45 minutes. PEI was added to a final concentration of 0.1% PEI. The mixture was stirred for an additional 30 minutes at 4° C. and centrifuged for 45 min at 5500 rpm in a RC3B centrifuge. The supernatant was loaded onto a DEFF column (4.4 cm×25 cm) equilibrated in 20 mM Tris, 6M Urea, pH 8. The DEFF flow through was adjusted to pH 5 with acetic acid and loaded onto a S-Sepharose Fast Flow column (4.4 cm×25 cm) equilibrated with 20 mM acetate, 6 M urea, pH 5. The NT-4/5 was eluted with 25 mM MOPSO, 0.5 M NaCl, pH 7.

The SSFF 0.5 M sodium chloride pool containing sulfonylated rhNT-4/5 was diluted to about 0.1 mg/ml protein and adjusted to 1M guanidine hydrochloride, 100 mM Tris, 20 mM glycine, 15% PEG-300, pH 8.3. The refolding of NT-4/5 was started by the addition of 2 to 4 mM cysteine. The refolding reaction was essentially complete within 24 hrs. Aeration with an inert gas, e.g. helium or nitrogen, to replace oxygen from the solution, can be optionally performed.

Example V

Isolation of Correctly Folded rhNT-4/5 From Conformational (Misfolded) Variants

The refold mixture of rhNT-4/5 of Example IV was dialyzed against a pH 4 to 5 solution overnight to remove guanidine and other reagents. To clarify the solution, the solution was either centrifuged for 45 minutes at 5000 rpm or passed through a 0.2 um filter.

The clarified supernatant, containing 0.5 to 5 grams of protein, was adjusted to pH 3 to 5 by addition of glacial acetic acid and was either loaded onto a C4 RP-HPLC column or stored frozen at −20° C. until ready for purification. In this exanple, the acidified and clarified solution was loaded onto a C4 RP-HPLC (3 cm×50 cm) column, to which resin the folded rhNT-4/5 bound. The correctly folded NT-4/5 was eluted using an acetonitrile gradient in a 0.05 Trifluoroacetic acid (TFA) solvent system: a 26 to 40% acetonitrile gradient (over a 95 minute period) in 0.05% TFA at a flow rate of 25 ml/min. Fractions were collected at 1 to 1.5 minute intervals (FIG. 8). Fractions were analyzed for correctly folded NT-4/5 by comparing elution time on an analytical C4 HPLC Vydac (0.21×15 cm) column to that of a correctly folded NT-4/5 standard (FIG. 9). Standard correctly folded, intact NT-4/5 typically eluted at 19 minutes at a flow rate of 2.5 ml per minute with a 0.5% TFA/acetonitrile buffer system. The fractions containing correctly folded rhNT-4/5 were pooled and pH-adjusted to pH 5 to 7. This pool of correctly folded rhNT-4/5 also contained carbamylated and N-terminal clipped forms of NT-4/5.

The preparative reverse-phase liquid chromatography resin is preferably a medium having a particle diameter of about 10–40 microns, a pore size of about 200–400 Angstroms, and a C4, C8, or C 18 alkyl group. More preferably, the resin has a particle diameter of about 15–40 micron and a pore size of about 300 Angstroms, and is a C4 silica medium.

Example VI

An Alternative Isolation of Correctly Folded rhNT-4/5 from Conformational (Misfolded) Variants The refolded rhNT-4/5 mixture of Example IV was concentrated approximately 10-fold using a Millipore-Pellicon ultrafiltration system with 20 square foot cellulose (or polysulfone or equivalent) membrane with a 10 kD-molecular weight cut-off. The concentrated mixture was either dialyzed overnight against 50 L of 50 mM acetate, pH 5.5, 50 mM NaCl or diafiltered into 50 mM acetate, 50 mM NaCl, pH 5.5, prior to filtering through a 0.2 micron membrane.

The filtered refolding mixture was adjusted to 2.5 M NaCl, 20 mM MOPSO, pH 7 and loaded onto a HIC column, phenyl Toyopearl 650M column (10 cm×19 cm), previously equilibrated in 2.5 M NaCl, 20 mM MOPSO, pH 7. The column was then washed with equilibration buffer. Some misfolded forms of the rhNT-4/5 molecule eluted in the flow-through fractions, while other misfolded forms were eluted at high concentrations of organic solvents such as 20 to 40% reagent alcohol. The correctly folded rhNT-4/5 was eluted from the phenyl column using 2 M sodium chloride, 10% reagent alcohol, pH 7 (FIG. 10). Other phenyl resins such as phenyl Sepharose can be used in place of the Toyopearl backbone. Salts discussed herein, including ammonium sulfate, citrate, acetate, and potassium chloride can be used. Depending on the salt used, the salt concentration is typically 1 M to 3 M, with 2.5 M NaCl being preferred for loading and 2M NaCl preferred for elution when organic solvent is present. Preferably, a lowering of the salt concentration is used to elute and separate a neurotrophin and its variants. In order to achieve elution, the salt concentration in the elution buffer is typically lower than that in the loading buffer, but it can be the same concentration when compensated for with organic solvent. In addition, the use of organic solvent has another advantage, as has been found herein, that the addition of an organic solvent improves the elution pattern by resulting in narrower peak profiles. In addition to ethanol, other organic solvents discussed herein can be used, including propanol, isopropanol, an d lower alkylene glycols, such as propylene glycol, ethylene glycol and hexylene glycol. The organic solvent at 5 to 25% (v/v), more preferably 5 to 20% (v/v), even more preferably 5 to 15%, will typically elute a correctly folded neurotrophin. The elution with organic solvent can be either gradient or step-wise. The pH range is preferably near neutral to slightly acidic, from pH 5 to 8, more preferably pH 5.5 to 7.5, and most preferably pH 7. Any of the buffers discussed herein, including MOPSO, MOPS, HEPES, phosphate, citrate, ammonium, acetate, can be used as long as they buffer at the desired pH.

Example VII

Purification of Correctly Folded rhNT-4/5 From Chemical Variants

Separation of correctly folded, intact rhNT-4/5 from its chemical variants, including carbamylated and N-terminal clipped forms of rhNT-4/5, was accomplished by high performance cation-exchange chromatography using SP-Sepharose HP resin or PolyCat a HPLC resin.

When the C4 RP-HPLC column was used to remove misfolded variants, the C4 HPLC pool was adjusted to pH 5 to 7 and loaded onto a 7 cm×19 cm SP-sepharose HP column equilibrated in 20 mM succinate, pH 6, 5% reagent alcohol, 0.2 M NaCl. The resin with bound NT-4/5 was washed with equilibration buffer. The bound rhNT-4/5 was eluted and separated from the carbamylated and N-terminal clipped forms using a 22 column volume (CV) gradient from 0.2 M NaCl to 0.4 M NaCl at pH 6 (i.e., salt gradient in equilibration buffer) (FIG. 11). Fractions containing NT-4/5 were pooled and formulated into 0.05 M acetate, pH 4 to 5. Intact rhNT-4/5 was identified and distinguished from the variants in the fractions preferably by analytical RP-HPLC, or by SDS-PAGE, as discussed herein, compared against standard.

Alternatively, the variant forms of NT-4/5 were removed by high performance cation-exchange HPLC on a polyaspartic acid column (PolyCAT a, PolyLC, Columbia, Md.) (9.4×200 mm) (FIG. 12). The C4 HPLC pool was adjusted to pH 5 to 6 and then loaded onto the Polycat a column. The chromatography conditions were: Buffer A was 20 mM phosphate, 5% acetonitrile, pH 6; Buffer B was 20 mM phosphate, 5% acetonitrile, 0.8 M KCl, pH 6. The rhNT-4/5 was eluted using a gradient of 25 to 60% Buffer B over 65 minutes (FIG. 12). Fractions were collected at 1 minute intervals and analyzed by analytical C4 HPLC as described above.

When HIC was used to remove misfolded variants (Example VI above), the correctly folded NT-4/5 pool was dialyzed overnight into 20 mM succinate, 0.1 M NaCl, 5% -reagent alcohol, pH 6 or ultrafiltered/diafiltered into the 20 mM succinate buffer. The dialyzed or UF/DF pool was then loaded onto a SP-Sepharose HP or PolyCAT a column as described above.

Formulation

Fractions containing correctly folded, intact NT-4/5 (from the SP-Sepharose HP or PolyCAT a HPLC step) were pooled and concentrated to 1 to 5 mg/ml in 20 mM acetate, pH 4 to 5 formulation buffer. Alternatively, the NT-4/5 was formulated using ultrafiltration/diafiltration.

The final bulk solution was analyzed by amino acid analysis, N-terminal sequence analysis, mass spectrometry, SDS-PAGE (FIG. 13) and biological assays a kinase receptor activation (KIRA) assay, which detects NT-4/5 activation of autophosphorylation of its tyrosine kinase receptor (trkB) located in a cell membrane, was used to characterize the purified rhNT-4/5. CHO cells expressing trkB with a gD tag were used. WO 95/14930, published Jun. 1, 1995, describes the KIRA assay and is incorporated herein by reference. The rhNT-4/5 had an EC50 of 12.6 ng/ml in this assay. Typically the EC50 of correctly, folded, intact NT-4/5, purified as described herein, is 5 to 30, more preferably 10 to 20.

Purity of rhNT-4/5 with respect to non-NT-4/5 proteins was typically 90 to 99 percent. Homogeneity of NT-4/5 with respect to carbamylated and N-terminal clipped variants was from 90 to 99 percent. Most typically, and preferably, the purity and homogeneity are 99% or greater.

Example VIII

Initial Purification, Refolding and Final Purification of rhNT-3 from Bacterial Inclusion Bodies To isolate the inclusion bodies from cell debris, the E. coli NT-3 paste (1 kg) was resuspended in 10 L of 100 mM sodium acetate, pH 5 using a rotary, mechanical dispersion device, for example a turrax. The cell suspension was passed through a microfluidizer three times at 6000 psi. The resulting homogenate was centrifuged in a Sorvall RC-3B centrifuge at 5000 rpm for 30 minutes.

NT-3 was isolated from the inclusion bodies as follows. The inclusion body pellets were suspended 100 mM Tris, 100 mM NaCl, 5 mM EDTA, 100 mM sodium sulfite, 10 mM sodium tetrathionate, 7.5 M urea, pH 8.3 (10 ml/gram of inclusion body) using a turrax at medium speed for about 10 min. The suspension was stirred for about one hour at 2–8° C. PEI (polyethyleneimine) was added to approximately 0.15% (final concentration) and stirred at 2–8° C. for 30 minutes. The mixture was centrifuged in a Sorval RC3B at 5000 rpm for abut 30 minutes. The supernatant was filtered with a Gelnan Preflow cartridge. The filtered supernatant was diluted with 3 volumes of S-Sepharose Fast Flow equilibration buffer (50 mM sodium acetate, 5 M urea, pH 5). The diluted filtered supernatant (conductivity less than 7 mS) is loaded onto an S-Sepharose FF column equilibrated with 50 mM sodium acetate, 5 M urea, pH 5.0. The column was first washed with 50 mM sodium acetate, 5M Urea, pH 5, followed by 50 mM MOPS, 5 M urea, 10 mM glycine, pH 7.0. Sulfitolyzed NT-3 was eluted from the column using a 10 column volume gradient from 0–0.6 M NaCl in 50 mM in 50 mM MOPS, 5 M urea, 10 mM glycine, pH 7.

Partially purified NT-3 was refolded by diluting the S-Sepharose FF pool to approximately .0.1 mg/ml protein in refolding buffer containing 0.1 M Tris, 2 M urea, 0.1 M NaCl, 15% PEG 300, 10 mM glycine, 25 mM ethanolamine, pH 9.1. Refolding was initiated by adding cysteine to approximately 5 mM and stirring for 2–5 days at 2–8° C. Optionally, the refolding buffer can be sparged with lie or Argon to reduce the oxygen concentration in the refolding solution.

The pH of the refolded pool was adjusted to pH 7, filtered and loaded onto a Macroprep High S cation-exchange chromatography column equilibrated in 50 mM HEPES, pH 7. After loading the pH adjusted refold pool to the Macroprep column, the column was first washed with 50 mM MOPS; pH 7 followed by 50 mM MOPS, 0.1 M TMAC, 0.3 M NaCl, pH 7. NT-3 was eluted with 50 mM MOPS, 0.25 M TMAC, 1.5 M NaCl, pH 7.

The Macroprep pool was then further purified on Phenyl Sepharose Fast Flow High Substitution column. The Phenyl column was equilibrated in 50 mM HEPES, 1.5 M NaCl, pH 7 and the macroprep pool was directly loaded to the Phenyl column. The column was washed with equilibration buffer and then the correctly refolded NT-3 was eluted using a 15 column volume gradient going from 50 mM HEPES, 1.5 M NaCl, pH 7 to 50 mM HEPES, 10% reagent alcohol, pH 7. Fractions were analyzed by either C4 HPLC or by SDS-PAGE and the fractions containing correctly-folded NT-3 were pooled.

The Phenyl pool was diluted to less than 25 mS (typically about 2 volumes with water) and loaded onto a SP-Sepharose HP column previously equilibrated in 25 mM MOPSO, pH 7. The column was first washed with equilibration buffer and NT-3 was eluted from the column using a 20 column volume gradient going from 0.35 M TMAC to 0.65 M TMAC in 25 mM MOPSO, pH 7. Fractions containing rhNT-3 (as judged by C4 HPLC assay) were pooled.

The SP-Sepharose HP pool was concentrated to about 1 mg/ml on a 10,000 molecular weight membrane and then diafiltered with 6 volume of 10 mM acetate, 140 mM NaCl, pH5.0.

What is claimed is:

1. A process to isolate a neurotrophin from a mixture comprising variants of that neurotrophin, wherein the process comprises eluting the neurotrophin from a hydrophobic interaction chromatography (HIC) resin with an elution buffer under conditions in which the neurotrophin separates from the variants.

2. The process of claim 1, wherein said HIC resin comprises a functional group selected from the group consisting of phenyl, octyl, propyl, alkoxy, butyl, and isoamyl functional groups.

3. The process of claim 2, wherein said HIC resin comprises a functional group selected from the group consisting of phenyl, octyl, propyl, alkoxy, and butyl functional groups.

4. The process of claim 2, wherein said HIC resin comprises a functional group selected from the group consisting of phenyl, octyl, and propyl functional groups.

5. The process of claim 2, wherein said HIC resin comprises a phenyl functional group.

6. The process of claim 5, wherein said HIC resin comprising a phenyl functional group is selected from the group consisting of Toyopearl(Ethylene glycol Methacrylate copolymer), agarose, and TSK Phenyl 5PW(Ethylene glycol methacrylate copolymer.

7. The process of claim 1, wherein said elution buffer comprises a salt selected from the group consisting of sodium chloride, sodium citrate, tetramethyl ammonium chloride, ammonium sulfate, ammonium citrate, ammonium acetate, and potassium chloride.

8. The process of claim 7, wherein said elution buffer comprises a salt concentration of about 0.5 M to about 3 M.

9. The process of claim 7, wherein said elution buffer comprises a salt concentration of about 0.5 M to about 2.5 M.

10. The process of claim 7, wherein said elution buffer comprises a salt concentration of about 0.8 M to about 1.5 M.

11. The process of claim 7, wherein said elution buffer comprises a salt concentration of about 1.0 M to about 2.5 M.

12. The process of claim 11, wherein said elution buffer comprises a salt concentration of about 1.25 M to about 1.75 M.

13. The process of claim 7, wherein said elution buffer comprises a salt concentration of about 1 M to about 3 M.

14. The process of claim 13, wherein said elution buffer has a pH of about pH 7.

15. The process of claim 7, wherein said elution buffer comprises a salt concentration of about 2 M salt, and includes an organic solvent.

16. The process of claim 15, wherein said elution buffer comprises about 10% alcohol, and has a pH of about pH 7.

17. The process of claim 1, wherein said elution buffer comprises an organic solvent.

18. The process of claim 17, wherein said organic solvent comprises an alcohol.

19. The process of claim 18, wherein said alcohol is an alcohol having 1 to 10 carbon atoms.

20. The process of claim 18, wherein said alcohol is selected from The group consisting of methanol, ethanol, iso-propanol, n-propanol, t-butanol, glycerol, propylene glycol, ethylene glycol, hexylene glycol, polypropylene glycol, polyethylene glycol, and lower alkylene glycols.

21. The process of claim 17, wherein said organic solvent comprises acetonitrile.

22. The process of claim 17, wherein said elution buffer comprises an organic solvent at a concentration of about 5 to about 25% (v/v).

23. The process of claim 22, wherein said organic solvent is at a concentration of about 5 to about 20% (v/v).

24. The process of claim 1, wherein said elution buffer has a pH of from about pH 5 to about pH 8.

25. The process of claim 24, wherein said elution buffer has a pH of from about pH 6 to about pH 8.

26. The process of claim 24, wherein said elution buffer has a pH of from about pH 6.5 to about pH 7.5.

27. The process of claim 24, wherein said elution buffer has a pH of about pH 7.

28. The process of claim 1, wherein said elution buffer comprises a buffering compound selected from the group consisting of ammonium, acetate, citrate, phosphate, succinate, 2-(N-Morpholino)ethanesulfonic acid (MES), N-2(-Acetamido)-2-iminodiacetic acid (ADA), BIS-TRIS Propane, piperazine-N,N'-bis(2-ethanesulfonic acid) (PIPES), N-(Carbamoylmethyl)-2-aminoethanesulfonic acid (ACES), imidazole, diethylmalonic acid, 3-(N-Morpholino)propanesulfonic acid (MOPS), 3-(N-Morpholino)-2-hydroxypropanesulfonic acid (MOPSO), 2-[(2-hydroxy-1,1 -bis[hydroxymethyl]ethyl)amino] ethanesulfonic acid (TES), Tris(hydroxymethyl) aminomethane (TRIS), N-2-Hydroxyethylpiperazine-N'-2-ethanesulfonic acid (HEPES), N-(2-hydroxyethyl) piperazine-N'-3-propanesuifonic acid (HEPPS), N-tris-hydroxymethyl)methylglycine (TRICINE), glycine amide, N,N-bis(2-hydroxyethyl)glycine (BICINE), glycylglycine, and borate buffers.

29. The process of claim 1, wherein said elution buffer comprises MOPSO.

* * * * *

SEQUENCE LISTING

<160> NUMBER OF SEQ ID NOS: 6

<210> SEQ ID NO 1
<211> LENGTH: 242
<212> TYPE: PRT
<213> ORGANISM: Homo sapien

<400> SEQUENCE: 1

Pro Met Ser Met Leu Phe Tyr Thr Leu Ile Thr Ala Phe Leu Ile Gly
1               5                   10                  15

Ile Gln Ala Glu Pro His Ser Glu Ser Asn Val Pro Ala Gly His Thr
            20                  25                  30

Ile Pro Gln Val His Trp Thr Lys Leu Gln His Ser Leu Asp Thr Ala
        35                  40                  45

Leu Arg Arg Ala Arg Ser Ala Pro Ala Ala Ile Ala Ala Arg Val
    50                  55                  60

Ala Gly Gln Thr Arg Asn Ile Thr Val Asp Pro Arg Leu Phe Lys Lys
65                  70                  75                  80

Arg Arg Leu Arg Ser Pro Arg Val Leu Phe Ser Thr Gln Pro Pro Arg
                85                  90                  95

Glu Ala Ala Asp Thr Gln Asp Leu Asp Phe Glu Val Gly Gly Ala Ala
            100                 105                 110

Pro Phe Asn Arg Thr His Arg Ser Lys Arg Ser Ser His Pro Ile
        115                 120                 125

Phe His Arg Gly Glu Phe Ser Val Cys Asp Ser Val Ser Val Trp Val
    130                 135                 140

Gly Asp Lys Thr Thr Ala Thr Asp Ile Lys Gly Lys Glu Val Met Val
145                 150                 155                 160

Leu Gly Glu Val Asn Ile Asn Asn Ser Val Phe Lys Gln Tyr Phe Phe
                165                 170                 175

Glu Thr Lys Cys Arg Asp Pro Asn Pro Val Asp Ser Gly Cys Arg Gly
            180                 185                 190

Ile Asp Ser Lys His Trp Asn Ser Tyr Cys Thr Thr Thr His Thr Phe
        195                 200                 205

Val Lys Ala Leu Thr Met Asp Gly Lys Gln Ala Ala Trp Arg Phe Ile
    210                 215                 220

Arg Ile Asp Thr Ala Cys Val Cys Val Leu Ser Arg Lys Ala Val Arg
225                 230                 235                 240

Arg Ala

<210> SEQ ID NO 2
<211> LENGTH: 121
<212> TYPE: PRT
<213> ORGANISM: Homo sapien

<400> SEQUENCE: 2

Pro Ser Ser Ser His Pro Ile Phe His Arg Gly Glu Phe Ser Val Cys
1               5                   10                  15

Asp Ser Val Ser Val Trp Val Gly Asp Lys Thr Thr Ala Thr Asp Ile
            20                  25                  30

Lys Gly Lys Glu Val Met Val Leu Gly Glu Val Asn Ile Asn Asn Ser
        35                  40                  45

Val Phe Arg Gln Tyr Phe Phe Glu Thr Lys Cys Arg Asp Pro Asn Pro
    50                  55                  60

-continued

Val Asp Ser Gly Cys Arg Gly Ile Asp Ser Lys His Trp Asn Ser Tyr
65                  70                  75                  80

Cys Thr Thr Thr His Thr Phe Val Lys Ala Leu Thr Met Asp Gly Lys
                85                  90                  95

Gln Ala Ala Trp Arg Phe Ile Arg Ile Asp Thr Ala Cys Val Cys Val
            100                 105                 110

Leu Ser Arg Lys Ala Val Arg Arg Ala
        115                 120

<210> SEQ ID NO 3
<211> LENGTH: 121
<212> TYPE: PRT
<213> ORGANISM: mouse

<400> SEQUENCE: 3

Pro Ser Ser Thr His Pro Val Phe His Met Gly Glu Phe Ser Val Cys
1               5                   10                  15

Asp Ser Val Ser Val Trp Val Gly Asp Lys Thr Thr Ala Thr Asp Ile
            20                  25                  30

Lys Gly Lys Glu Val Thr Val Leu Ala Glu Val Asn Ile Asn Asn Ser
        35                  40                  45

Val Phe Arg Gln Tyr Phe Phe Glu Thr Lys Cys Arg Ala Ser Asn Pro
    50                  55                  60

Val Glu Ser Gly Cys Arg Gly Ile Asp Ser Lys His Trp Asn Ser Tyr
65                  70                  75                  80

Cys Thr Thr Thr His Thr Phe Val Lys Ala Leu Thr Thr Asp Glu Lys
                85                  90                  95

Gln Ala Ala Trp Arg Phe Ile Arg Ile Asp Thr Ala Cys Val Cys Val
            100                 105                 110

Leu Ser Arg Lys Ala Thr Arg Arg Gly
        115                 120

<210> SEQ ID NO 4
<211> LENGTH: 119
<212> TYPE: PRT
<213> ORGANISM: Homo sapien

<400> SEQUENCE: 4

Pro His Ser Asp Pro Ala Arg Arg Gly Glu Leu Ser Val Cys Asp Ser
1               5                   10                  15

Ile Ser Glu Trp Val Thr Ala Ala Asp Lys Lys Thr Ala Val Asp Met
            20                  25                  30

Ser Gly Gly Thr Val Thr Val Leu Glu Lys Val Pro Val Ser Lys Gly
        35                  40                  45

Gln Leu Lys Gln Tyr Phe Tyr Glu Thr Lys Cys Asn Pro Met Gly Tyr
    50                  55                  60

Thr Lys Glu Gly Cys Arg Gly Ile Asp Lys Arg His Trp Asn Ser Gln
65                  70                  75                  80

Cys Arg Thr Thr Gln Ser Tyr Val Arg Ala Leu Thr Met Asp Ser Lys
                85                  90                  95

Lys Arg Ile Gly Trp Arg Phe Ile Arg Ile Asp Thr Ser Cys Val Thr
            100                 105                 110

Leu Thr Ile Lys Arg Gly Arg
        115

<210> SEQ ID NO 5
<211> LENGTH: 120

-continued

<212> TYPE: PRT
<213> ORGANISM: Homo sapien

<400> SEQUENCE: 5

Pro Tyr Ala Glu His Lys Ser His Arg Gly Glu Tyr Ser Val Cys Asp
1               5                   10                  15

Ser Glu Ser Leu Trp Val Thr Asp Lys Ser Ser Ala Ile Asp Ile Arg
            20                  25                  30

Gly His Gln Val Thr Val Leu Gly Glu Ile Lys Thr Gly Asn Ser Pro
            35                  40                  45

Val Lys Gln Tyr Phe Tyr Glu Thr Arg Cys Lys Glu Ala Arg Pro Val
    50                  55                  60

Lys Asn Gly Cys Arg Gly Ile Asp Asp Lys His Trp Asn Ser Gln Cys
65                  70                  75                  80

Lys Thr Ser Gln Thr Tyr Val Arg Ala Leu Thr Ser Glu Asn Asn Lys
                85                  90                  95

Leu Val Gly Trp Arg Trp Ile Arg Ile Asp Thr Ser Cys Val Ser Ala
            100                 105                 110

Leu Ser Arg Lys Ile Gly Arg Thr
            115                 120

<210> SEQ ID NO 6
<211> LENGTH: 130
<212> TYPE: PRT
<213> ORGANISM: Homo sapien

<400> SEQUENCE: 6

Gly Val Ser Glu Thr Ala Pro Ala Ser Arg Arg Gly Glu Leu Ala Val
1               5                   10                  15

Cys Asp Ala Val Ser Gly Trp Val Thr Asp Arg Arg Thr Ala Val Asp
            20                  25                  30

Leu Arg Gly Arg Glu Val Glu Val Leu Gly Glu Val Pro Ala Ala Gly
            35                  40                  45

Gly Ser Pro Leu Arg Gln Tyr Phe Phe Glu Thr Arg Cys Lys Ala Asp
    50                  55                  60

Asn Ala Glu Glu Gly Gly Pro Gly Ala Gly Gly Gly Cys Arg Gly
65                  70                  75                  80

Val Asp Arg Arg His Trp Val Ser Glu Cys Lys Ala Lys Gln Ser Tyr
                85                  90                  95

Val Arg Ala Leu Thr Ala His Ala Gln Gly Arg Val Gly Trp Arg Trp
            100                 105                 110

Ile Arg Ile Asp Thr Ala Cys Val Cys Thr Leu Leu Ser Arg Thr Gly
            115                 120                 125

Arg Ala
    130